(12) United States Patent
Fruehauf et al.

(10) Patent No.: US 6,511,806 B1
(45) Date of Patent: Jan. 28, 2003

(54) METHODS FOR CANCER PROGNOSIS AND DIAGNOSIS

(75) Inventors: John Fruehauf, Tustin, CA (US); Eugene Mechetner, Irvine, CA (US)

(73) Assignee: Oncotech, Inc., Tustin, CA (US)

( * ) Notice: Subject to any disclaimer, the term of this patent is extended or adjusted under 35 U.S.C. 154(b) by 0 days.

(21) Appl. No.: 09/705,320

(22) Filed: Nov. 3, 2000

Related U.S. Application Data

(60) Provisional application No. 60/163,340, filed on Nov. 3, 1999.

(51) Int. Cl.[7] .......................... C12Q 1/68; C12P 21/06; G01N 33/53
(52) U.S. Cl. .......................... 435/6; 435/69.1; 435/7.2
(58) Field of Search .................... 435/6, 69.1, 7.2, 435/7.23

(56) References Cited

U.S. PATENT DOCUMENTS

| | | | | |
|---|---|---|---|---|
| 4,996,145 A | * | 2/1991 | Wesenthal | 435/7.23 |
| 5,776,747 A | | 7/1998 | Aebischer et al. | |
| 5,994,088 A | * | 11/1999 | Mechetner et al. | 435/7.21 |
| 6,004,755 A | | 12/1999 | Wang et al. | |
| 6,040,138 A | * | 3/2000 | Lockhart et al. | 435/6 |

FOREIGN PATENT DOCUMENTS

WO  WO 99/50401 A  7/1999

OTHER PUBLICATIONS

Mechetner E et al. Levels of multidrug resistance (MDR1) P–glycoprotein expression by human breast cancer correlate with in vitro resistance to taxol and doxorubin. Clin.Cancer Res., 4: 389–398, 1998.*
Lebow L T et al., Natural Immunity and Cell Growth Regulation, vol. 5, No. 5, 1986, pp. 221–237.
Orfao Alberto et al., Cytometry, vol. 17, No. 4, 1994, pp. 332–339.
Borgiani L et al., Pathologica (Genoa) vol. 86, No. 4, 1994, pp. 356–359.
Pepper C et al., British Journal of Cancer, Lond–on, GB, vol. 76, No. 7, 1997, pp. 935–938.
Chen H.W. and Huang H.C., British Journal of Pharmacology, vol. 124, No. 6, Jul. 1998.
Seidl J et al. Cytometry, vol. 36, No. 2, Jun. 1, 1999.
Gudkov et al., 1993 Proc. Natl. Acad. Sci. USA 90:3231–3235.
Maino et al., 1995, Cytometry, 20:127–133.
Kern et al., 1990, J. Nat. Cancer Inst. 82:582–588.

* cited by examiner

*Primary Examiner*—Jeffrey Fredman
*Assistant Examiner*—Suryaprabha Chunduru
(74) *Attorney, Agent, or Firm*—McDonnell Boehnen Hulbert & Berghoff

(57) ABSTRACT

The invention provides methods for prognosis, diagnosis, staging and disease progression in human cancer patients related to expression levels of a plurality of genes that are differentially expressed in chemotherapeutic drug resistant and drug sensitive tumor cells.

16 Claims, 15 Drawing Sheets

SAMPLE ID:SKBR3 SORT ISOTYPE  GATE :G1
MARKER  %GATED  MEAN
ALL     100.00  5.24
M1      0.00    ***

SAMPLE ID:SKBR3 SORT  GATE :G1
MARKER  %GATED  MEAN
ALL     100.00  2426.91
M1      84.99   2753.16

SAMPLE ID:SKBR3 +POST SORT  GATE :G1
MARKER  %GATED  MEAN
ALL     100.00  3389.98
M1      97.92   3455.55

1.2% AGAROSE GEL
~1 μg TOTAL RNA/LANE

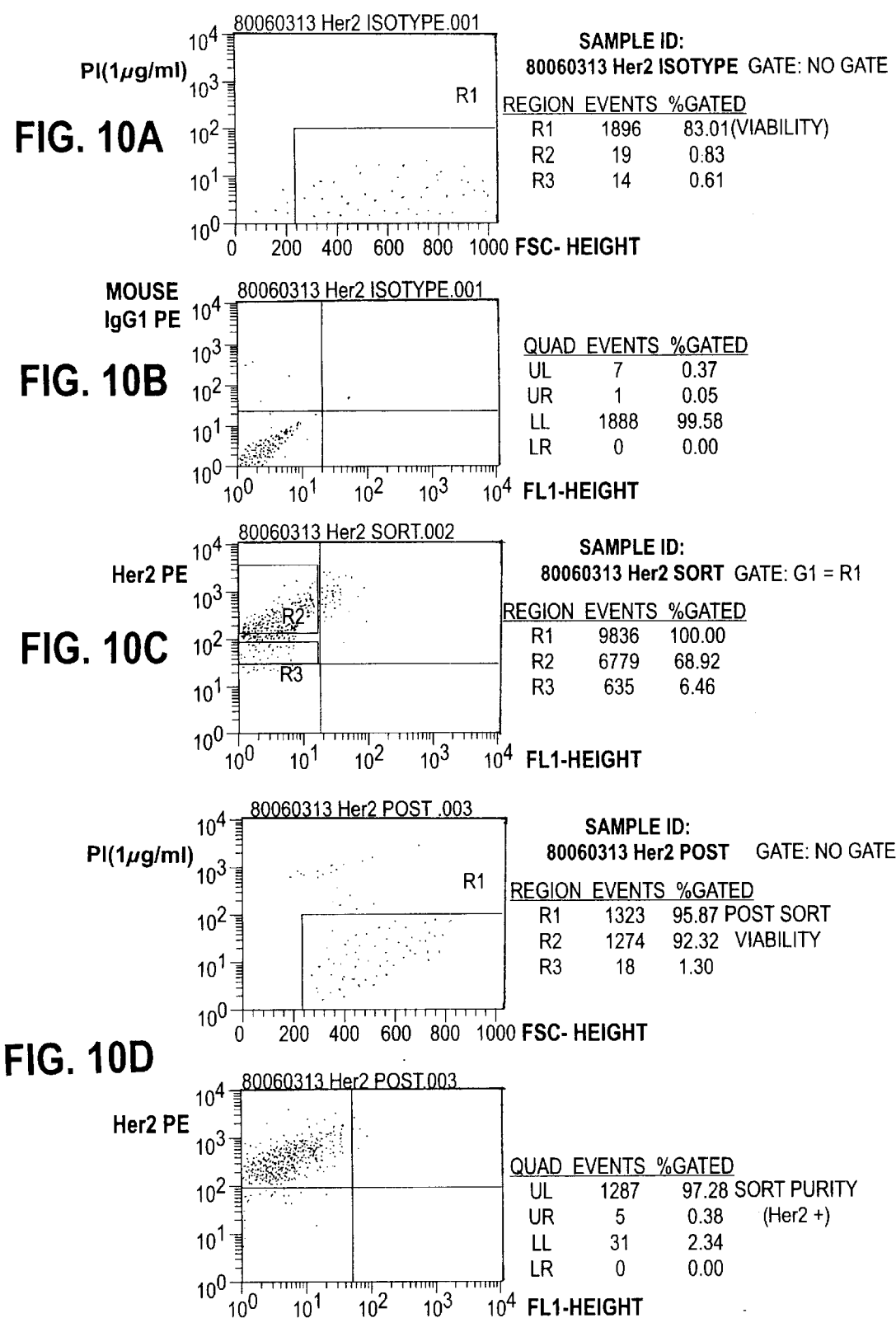

SAMPLE ID: 899 isotype    ACQUISITION DATE: 24
GATE: NO GATE

| REGION | % GATED |
|---|---|
| R1 | 91.52 |

SAMPLE ID: 899 Her-2    ACQUISITION DATE: 24
GATE: G1

| MARKER | % GATED |
|---|---|
| ALL | 100.00 |
| M1 | 96.24 |

METHODS FOR CANCER PROGNOSIS AND DIAGNOSIS

This is a Continuation of prior application Ser. No. 60/163,340 filed Nov. 3, 1999.

BACKGROUND OF THE INVENTION

1. Field of the Invention

The invention relates to cancer diagnosis and treatment, and specifically to the determination of a drug resistance phenotype in neoplastic cells from cancer patients. The invention specifically relates to the separation of chemotherapeutic drug resistant neoplastic cells from drug sensitive neoplastic cells and stromal cells. The invention in particular relates to the identification of genes that are differentially expressed in chemotherapeutic drug resistant neoplastic cells compared with the expression of these genes in drug sensitive neoplastic cells. As part of this identification, the invention provides a pattern of expression from a selected number of identified genes, the expression of which is increased or decreased in chemotherapeutic drug resistant neoplastic cells. The invention provides methods for identifying such genes and expression patterns of such genes and using this information to make clinical decisions on cancer treatment, especially chemotherapeutic drug treatment of cancer patients.

2. Summary of the Related Art

Cancer remains one of the leading causes of death in the United States. Clinically, a broad variety of medical approaches, including surgery, radiation therapy and chemotherapeutic drug therapy are currently being used in the treatment of human cancer (see the textbook *CANCER: Principles & Practice of Oncology*, 2d Edition, De Vita et al., eds., J. B. Lippincott Company, Philadelphia, Pa., 1985). However, it is recognized that such approaches continue to be limited by a fundamental inability to accurately predict the likelihood of clinically successful outcome, particularly with regard to the sensitivity or resistance of a particular patient's tumor to a chemotherapeutic agent or combinations of chemotherapeutic agents.

A broad variety of chemotherapeutic agents are used in the treatment of human cancer. These include the plant alkaloids vincristine, vinblastine, vindesine, and VM-26; the antibiotics actinomycin-D, doxorubicin, daunorubicin, mithramycin, mitomycin C and bleomycin; the antimetabolites methotrexate, 5-fluorouracil, 5-fluorodeoxyuridine, 6-mercaptopurine, 6-thioguanine, cytosine arabinoside, 5-aza-cytidine and hydroxyurea; the alkylating agents cyclophosphamide, melphalan, busulfan, CCNU, MeCCNU, BCNU, streptozotocin, chlorambucil, bis-diamminedichloroplatinum, azetidinylbenzoquinone; and the miscellaneous agents dacarbazine, mAMSA and mitoxantrone (DeVita et al., Id.). However, some neoplastic cells become resistant to specific chemotherapeutic agents, in some instances even to multiple chemotherapeutic agents, and some tumors are intrinsically resistant to certain chemotherapeutic agents. Such drug resistance or multiple drug resistance can theoretically arise from expression of genes that confer resistance to the agent, or from lack of expression of genes that make the cells sensitive to a particular anticancer drug. One example of the former type is the multidrug resistance gene, MDR1, which encodes an integral plasma membrane protein termed P-glycoprotein that is an non-specific, energy-dependent efflux pump. (See Roninson (ed)., 1991, *Molecular and Cellular Biology of Multidrug Resistance in Tumor Cells*, Plenum Press, N.Y., 1991; Gottesman et al., 1991, in *Biochemical Bases for Multidrug Resistance in Cancer*, Academic Press, N.Y., Chapter 11 for reviews). Examples of the latter type include topoisomerase II, the expression of which makes cells sensitive to the anticancer drug etoposide. Decreased expression of this enzyme makes neoplastic cells resistant to this drug. (See Gudkov et al., 1993, *Proc. Natl. Acad. Sci. USA* 90:3231–3235). Although these are just single examples of the way that modulation of gene expression can influence chemotherapeutic drug sensitivity or resistance in neoplastic cells, these examples demonstrate the diagnostic and prognostic potential for identifying genes the expression of which (or the pattern of gene expression modulation thereof) are involved in mediating the clinical effectiveness of anticancer drug treatment.

Thus, there is a need in this art for developing methods for identifying genes and gene expression patterns that are predictive of the clinical effectiveness of anticancer drug treatment therapies, in order to make more informed decisions for treating individual cancer patients with anticancer drugs having greatest likelihood of producing a positive outcome.

SUMMARY OF THE INVENTION

The present invention provides methods identifying genes and gene expression patterns that are predictive of the clinical effectiveness of anticancer drug treatment therapies.

In a first aspect the invention provides a method for separating living neoplastic cells from dead cells and living stromal cells in a mixed population of cells from a tumor sample, the method comprising the steps of:
  a) contacting the mixed population of cells with a vital stain or fluorescent dye;
  b) contacting the mixed population of cells with a detectably-labeled immunological reagent that specifically binds to neoplastic cells; and
  c) selecting the cells in the mixed population of step (b) that are not stained with the vital stain and that bind the immunological reagent.

In a preferred embodiment, the vital stain is propidium iodide. Most preferably, the immunological reagent is a tumor-specific antibody that is detectably labeled with a fluorescent label and the cells are separated by fluorescence activated cell sorting. In certain embodiments, the tumor sample is a solid tumor sample and the mixed cell population is a disaggregated tumor sample. In other embodiments, the tumor sample is a hematopoietic tumor sample and the mixed cell population is a nucleated hematopoietic cell sample.

In a second aspect, the invention provides a method for separating living neoplastic cells that are resistant to a cytotoxic compound from dead cells, living stromal cells and living neoplastic cells that are sensitive to the cytotoxic compound in a mixed population of cells from a tumor sample, the method comprising the steps of:
  a) contacting the mixed population of cells with the cytotoxic compound for a time and at a concentration wherein the stromal cells and neoplastic cells that are sensitive to the cytotoxic compound undergo apoptosis;
  b) contacting the mixed population of step (a) with a vital stain or fluorescent dye;
  c) contacting the mixed population of cells of step (b) with a discrimination compound that specifically binds to apoptotic cells;
  d) contacting the mixed cell population of step (c) with a detectably-labeled immunological reagent that specifically binds to the apoptotic cell discrimination compound; and e) selecting the cells in the mixed population of step (c) that are not stained with the vital stain and that do not bind the immunological reagent.

In a preferred embodiment, the vital stain is propidium iodide. Most preferably, the apoptosis discrimination reagent is Annexin V and the immunological reagent is an Annexin V-specific antibody that is detectably labeled with a fluorescent label, wherein the cells are separated by fluorescence activated cell sorting. In preferred embodiments, the mixed population is contacted with the cytotoxic compound under in vitro cell culture conditions whereby the cells cannot attach to a solid substrate. In certain embodiments, the tumor sample is a solid tumor sample and the mixed cell population is a disaggregated tumor sample. In other embodiments, the tumor sample is a hematopoietic tumor sample and the mixed cell population is a nucleated hematopoietic cell sample.

In yet a third aspect, the invention provides a method for detecting a gene expression profile of living neoplastic cells that are resistant to a cytotoxic compound and distinguishing such a profile from the gene expression profile of living neoplastic cells that are sensitive to the cytotoxic compound in a mixed population of cells from a tumor sample, the method comprising the steps of:

a) contacting the mixed population of cells with the cytotoxic compound for a time and at a concentration wherein the neoplastic cells that are sensitive to the cytotoxic compound undergo apoptosis;

b) contacting the mixed population of step (a) with a vital stain or fluorescent dye;

c) contacting the mixed population of cells of step (b) with a discrimination compound that specifically binds to apoptotic cells;

d) contacting the mixed cell population of step (c) with a detectably-labeled immunological reagent that specifically binds to the apoptotic cell discrimination compound; and e) separating the cells in the mixed population of step (d) that are not stained with the vital stain from the cells that are stained with the vital stain;

f) separating the cells in the mixed population of step (e) that are not stained with the vital stain and that do not bind the immunological reagent from the cells in the mixed population of step (c) that are not stained with the vital stain and that do bind the immunological reagent;

g) isolating cellular RNA from the each of the separated cells selected in step (f);

h) preparing detectably-labeled cDNA from the cellular RNA isolated in step (g);

i) hybridizing each of the CDNA preparations prepared in step (h) to a gene array comprising at least 4000 eukaryotic genes;

j) detecting a pattern of gene expression for hybridization of each of the cDNA preparations prepared from the mRNA isolated from the cells selected in step (f); and k) comparing the pattern of gene expression detected in step (j) from ahybridization of the microarray with cDNA from cells that are not stained with the vital stain and that do not bind the immunological reagent with a pattern of gene expression obtained by hybridizing cDNA prepared from cells that are not stained with the vital stain and that do bind the immunological reagent.

In a preferred embodiment, the vital stain is propidium iodide. Most preferably, the apoptosis discrimination reagent is Annexin V and the immunological reagent is an Annexin V-specific antibody that is detectably labeled with a fluorescent label, wherein the cells are separated by fluorescence activated cell sorting. In preferred embodiments, the mixed population is contacted with the cytotoxic compound under in vitro cell culture conditions whereby the cells cannot attach to a solid substrate. In certain embodiments, the tumor sample is a solid tumor sample and the mixed cell population is a disaggregated tumor sample. In other embodiments, the tumor sample is a hematopoietic tumor sample and the mixed cell population is a nucleated hematopoietic cell sample.

In another aspect, the invention provides a diagnostic assay for characterizing tumors and neoplastic cells, particularly human neoplastic cells, wherein cytotoxic drug resistant, and most preferably chemotherapeutic drug resistant neoplastic cells, by the differential expression of genes and patterns of genes whereby the drug resistant phenotype is associated with, identified by and can be diagnosed on the basis thereof. This diagnostic assay comprises detecting, qualitatively or preferably quantitatively, the expression levels of a gene or a plurality of genes comprising a pattern of expression of genes and making a diagnosis of drug resistance on the basis of this expression pattern of a gene or plurality of genes. In a preferred embodiment, the invention provides methods for identifying a gene or a plurality of genes showing differential gene expression in drug resistant neoplastic cells. In other preferred embodiments, the invention provides methods for detecting expression of a gene or a plurality of genes comprising a pattern of gene expression in drug resistant neoplastic cells. In still other embodiments, the invention provides these methods for a multiplicity of chemotherapeutic drugs to determine drugs for which a patient's tumor is not resistant or shows a minimal level of resistance.

In another embodiment, the invention provides a starting point for in vitro drug screening and rational design of pharmaceutical products that are more effective antineoplastic agents. By identifying a pattern of differential gene expression related to drug resistance, strategies can be developed for creating pharmaceutical products that are improved chemotherapeutic agents to more effectively treat neoplastic disease.

It is an advantage of the methods of this invention that pure neoplastic cell populations from solid and hematopoietic tumors, both malignant and benign, can be obtained separated from stromal cells, infiltrating non-neoplastic hematopoietic cells and other tumor components. This feature of the inventive methods are advantageous because the presence of such contaminating, non-neoplastic cells in tumor sample preparations confounds analyses directed at detecting neoplastic cell-specific properties, such as patterns of gene expression as disclosed herein. It is also an advantage of the present inventive methods that drug-resistant and drug-sensitive neoplastic cells can be separated from pure neoplastic cell populations. As a result, RNA preparations specific for drug-resistant and drug-sensitive neoplastic cells are obtained that can be used to identify genes, and patterns of genes, that are differentially expressed in drug-resistant and drug-sensitive neoplastic cells. In addition, the methods of the invention as provided permit drug-resistant and drug-sensitive neoplastic cells to be simultaneously treated with cytotoxic drugs in the same mixed cell culture, thereby avoiding experimental variability.

Specific preferred embodiments of the present invention will become evident from the following more detailed description of certain preferred embodiments and the claims.

BRIEF DESCRIPTION OF THE DRAWINGS

FIG. 5A shows cell scatter in the lower left quadrant, FIG. 5B shows separation into living, drug-resistant neoplastic cells (R2 in the lower left quadrant), apoptotic, drug-sensitive cells (R1 in the lower right quadrant) and dying, drug-sensitive cells (in the upper right quadrant). FIG. 5C provides confirmation of the separation of apoptotic, drug-sensitive cells (the sorted cells resort into the lower right quadrant). FIG. 5D provides confirmation of the separation of living, drug-resistant cells (the sorted cells resort into the lower left quadrant).

FIG. 6A shows that the majority of the cells remained viable, and FIG. 6B shows that the cells bound HER2.

FIGS. 10A through 10D are fluorescence-activated cell sorting (FACS) profiles of cells from a human breast tumor sample. FIG. 10A shows cell viability, FIG. 10B shows negligible non-specific isotypic antibody binding, FIG. 10C shows separation of the population into apoptotic, drug-sensitive neoplastic cells (R2) and living, drug-resistant neoplastic cells (R3). FIG. 10D provides confirmation that 96% of the sorted cells are viable (FIG. 10D, top) and that 97% of the sorted cells were HER2 positive (FIG. 9D, bottom).

FIG. 11A shows that 91.5% of the cells remained viable, and FIG. 11B shows that 96.2% of the cells bound HER2.

FIG. 12A shows cell scatter (99.8% in the lower left quadrant), FIG. 12B shows separation into living, drug-resistant neoplastic cells (R2; 14.6% of cells in the lower left quadrant), apoptotic, drug-sensitive cells (R1; 40.5% in the lower right quadrant) and dying, drug-sensitive cells (44.7% in the upper right quadrant). FIG. 12C provides confirmation of the separation of apoptotic, drug-sensitive cells (93.3% of the sorted cells resort into the lower right quadrant). FIG. 12D provides confirmation of the separation of living, drug-resistant cells (92.25% of the sorted cells resort into the lower left quadrant).

DETAILED DESCRIPTION OF THE PREFERRED EMBODIMENTS

Figure 1:
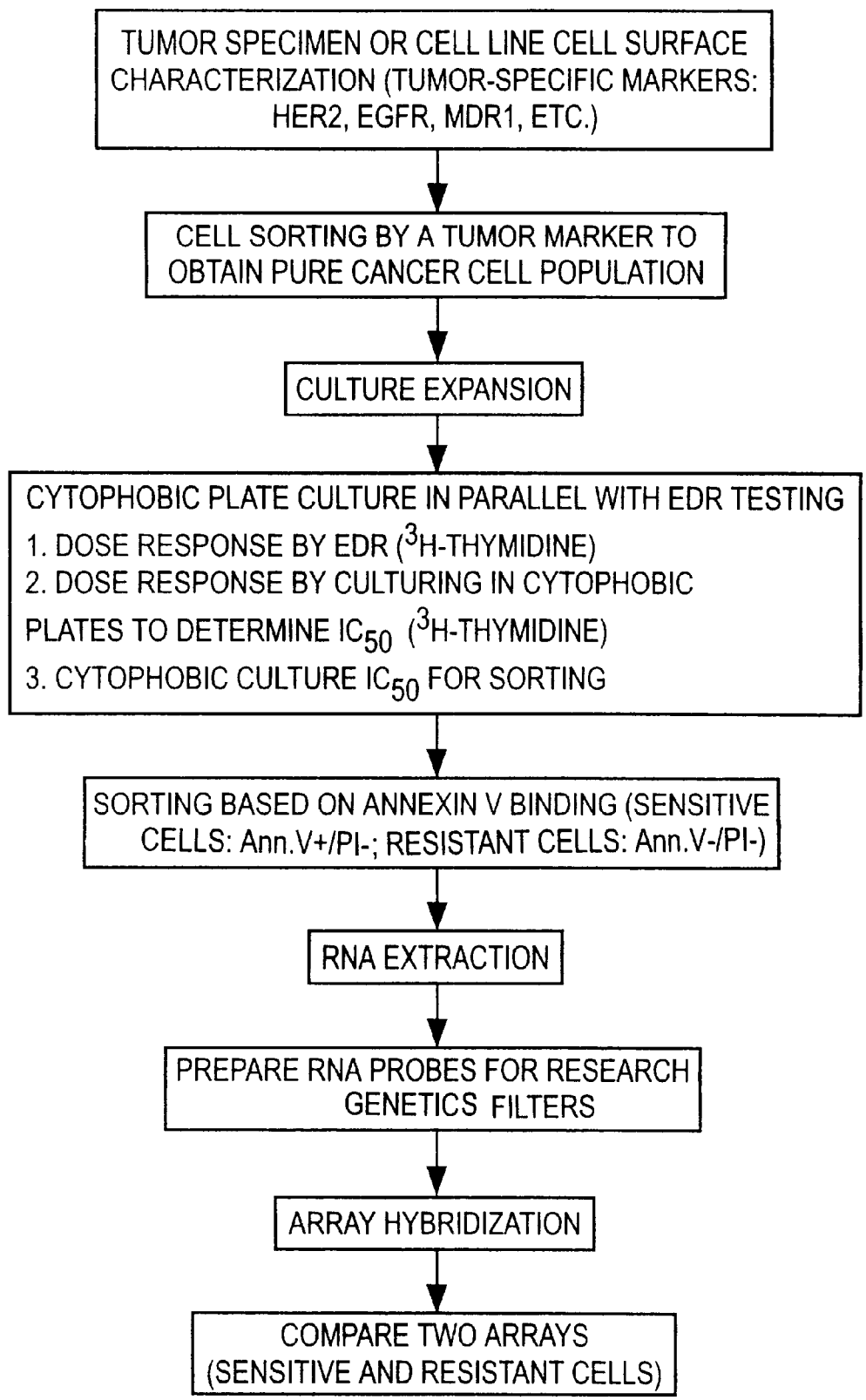
FIG. 1 is a schematic flowchart illustrating an embodiment of the methods of the invention showing how drug-resistant neoplastic cell-specific mRNA is used to probe a gene expression micro array.

The present invention provides a method for making a prognosis about disease course in a human cancer patient. For the purposes of this invention, the term "prognosis" is intended to encompass predictions and likelihood analysis of disease progression, particularly tumor recurrence, metastatic spread and disease relapse. The prognostic methods of the invention are intended to be used clinically in making decisions concerning treatment modalities, including therapeutic intervention, diagnostic criteria such as disease staging, and disease monitoring and surveillance for metastasis or recurrence of neoplastic disease.

The methods of the invention are preferably performed using human cancer patient tumor samples, most preferably samples preserved, for example in paraffin, and prepared for histological and immunohistochemical analysis.

For the purposes of this invention, the term "tumor sample" is intended to include resected solid tumors, biopsy material, pathological specimens, bone marrow aspirates, and blood samples comprising neoplastic cells of hematopoietic origin, as well as benign tumors, particularly tumors of certain tissues such as brain and the central nervous system. One of ordinary skill will appreciate that samples derived from solid tumors will require combinations of physical and chemical/enzymatic disaggregation to separate neoplastic cells from stromal cells and infiltrating hematopoietic cells, while hematopoietic tumor samples including leukemias and lymphomas will be obtained as mixed cell populations in blood, serum or plasma, and will require separation from non-neoplastic components thereof, particularly from red blood cells that can be lysed by treatment with hypotonic solutions and from other nucleated cells, whereby separation is achieved by differential centrifugation and other methods known in the art.

Living cells are separated from dying cells, dead cells and cell debris, and drug sensitive and drug resistant cells are separated from each other and from non-neoplastic cells according to the methods of the invention by cell sorting methods, most preferably fluorescence-activated cell sorting (FACS). Separation of living cells from dying cells, dead cells and cell debris is facilitated by contacting mixed cell populations with a vital stain, preferably a fluorescent vital stain, such as propidium iodide (PI) and ethidium bromide (EtBr). Separation of drug sensitive and drug resistant cells from one another and from non-neoplastic cells using reagents, most preferably immunological agents, that discriminate between such cells. In particular, drug resistant neoplastic cells are separated from drug sensitive neoplastic cells after incubation with a cytotoxic amount of a chemotherapeutic drug by contacting the mixed cell population with a discrimination compound that specifically binds to apoptotic cells, and separation is achieved using reagents, most preferably immunological agents, that specifically binds to the discrimination compound. In preferred embodiments, the discrimination compound is an annexin, most preferably annexin V or antibodies directed against caspases.

For the purposes of this invention, the term "immunological reagents" is intended to encompass antisera and antibodies, particularly monoclonal antibodies, as well as fragments thereof (including F(ab), F(ab)$_2$, F(ab)' and F$_v$ fragments). Also included in the definition of immunological reagent are chimeric antibodies, humanized antibodies, and recombinantly-produced antibodies and fragments thereof, as well as aptamers (i.e., oligonucleotides capable of interacting with target molecules such as peptides). Immunological methods used in conjunction with the reagents of the invention include direct and indirect (for example, sandwich-type) labeling techniques, immunoaffinity columns, immunomagnetic beads, fluorescence activated cell sorting (FACS), enzyme-linked immunosorbent assays (ELISA), and radioimmune assay (RIA), most preferably FACS. For use in these assays, the neoplastic immunological reagents can be labeled, using fluorescence, antigenic, radioisotopic or biotin labels, among others, or a labeled secondary or tertiary immunological detection reagent can be used to detect binding of the neoplastic immunological reagents (i.e., in secondary antibody (sandwich) assays).

Examples of immunological reagents useful in the practice of this invention include antibodies, most preferably monoclonal antibodies, that recognize tumor antigens such as CA15-3 (breast cancer), CA19-9 (gastrointestinal cancer), CA125 (ovarian cancer), CA242 (gastrointestinal cancer), p53 (colorectal cancer), prostate-specific acid phosphatase (prostate cancer), Rb (retinoblastoma), CD56 (small cell lung cancer), prostate-specific antigen (prostate cancer), carcinoembryonic antigen (CEA), melanoma antigen and melanoma-associated antigens (melanoma), mucin-1 (carcinoma), HER2 (breast cancer), and EGFR (breast and ovarian cancer).

The immunological reagents of the invention are preferably detectably-labeled, most preferably using fluorescent labels that have excitation and emission wavelengths adapted for detection using commercially-available instruments such as and most preferably fluorescence activated cell sorters. Examples of fluorescent labels useful in the practice of the invention include phycoerythrin (PE), fluorescein isothiocyanate (FITC), rhodamine (RH), Texas Red (TX), Cy3, Hoechst 33258, and 4',6-diamidino-2-phenylindole (DAPI). Such labels can be conjugated to immunological reagents, such as antibodies and most preferably monoclonal antibodies using standard techniques (Maino et al., 1995, Cytometry 20:127–133).

As used herein, the terms "microarray," "bioarray," "biochip" and "biochip array" refer to an ordered spatial arrangement of immobilized biomolecular probes arrayed on a solid supporting substrate. Preferably, the biomolecular probes are immobilized on second linker moieties in contact with polymeric beads, wherein the polymeric beads are immobilized on first linker moieties in contact with the solid supporting substrate. Biochips, as used in the art, encompass substrates containing arrays or microarrays, preferably ordered arrays and most preferably ordered, addressable arrays, of biological molecules that comprise one member of a biological binding pair. Typically, such arrays are oligonucleotide arrays comprising a nucleotide sequence that is complementary to at least one sequence that may be or is expected to be present in a biological sample. Alternatively, and preferably, proteins, peptides or other small molecules can be arrayed in such biochips for performing, inter alia, immunological analyses (wherein the arrayed molecules are antigens) or assaying biological receptors (wherein the arrayed molecules are ligands, agonists or antagonists of said receptors). Useful microarrays for detecting differential gene expression between chemotherapeutic drug sensitive and resistant neoplastic cells are described, inter alia, in U.S. Pat. No. 6,040,138 to Lockhart et al. (commercially-available from Affymetrix, Inc., Santa Clara, Calif.) and U.S. Pat. No. 6,004,755 to Wang (commercially-available from Incyte Inc., Palo Alto, Calif.) and are also commercially available, inter alia, from Research Genetics (Huntsville, Ala.).

The practice of one embodiment of the invention is shown in FIG. 1. A tumor sample or a tumor cell line is harvested and pure cancer cell population obtained by FACS sorting using fluorescently-labeled antibodies specific for neoplastic cell markers (such as HER2, EGFR or MDR1). The sorted pure cancer cell population is then expanded by growth in cell culture to provide sufficient cells for separation into drug-sensitive and drug-resistant populations. Drug resistant cells are separated from drug sensitive cells by culture in increasing concentrations of cytotoxic drugs, and the degree of drug resistance quantitated by growing the cells in a cell proliferation-specific detectable label (such as tritiated thymidine) for a terminal portion of each cell culture experiment. IC$_{50}$ values can be established by performing this assay in cytophobic plates that inhibit cell attachment (and therefore prevent proliferation of non-neoplastic cells). Finally, cell culture at the IC$_{50}$ concentration of the cytotoxic drug in cytophobic plates is used to prepare neoplastic cells for flow sorting. It will be recognized that a significant advantage of these methods is that a mixed population of drug-sensitive and drug-resistant cells are treated simultaneously under exactly identical conditions of cell culture and drug treatment and then analyzed after separation based on their differential drug resistance characteristics.

Drug sensitive neoplastic cells are separated from drug resistant neoplastic cells, most preferably using fluorescence-activated cell sorting. Cells cultured in cytotoxic drug at the IC$_{50}$ are stained with a fluorescent vital stain such as propidium iodide and contacted with an apoptosis-specific, discrimination compound and with a fluorescently-labeled immunological reagent that specifically labels the apoptotic, drug sensitive neoplastic cells. In a preferred embodiment, the discrimination reagent Annexin V, which binds to phosphatidylserine exposed by apoptosis in drug sensitive cells and does not bind to drug resistant neoplastic cells. FACS analysis separates the drug resistant, living cells from cell debris, dead cells (such as stromal cells) and drug-sensitive neoplastic cells. It is also an advantage of the inventive methods that FACS sorting can discriminate between drug sensitive neoplastic cells (typically caused to be apoptotic as a result of cytotoxic drug treatment), drug resistant neoplastic cells and dead or dying cells by gating the cell sorter to perform simultaneous discrimination between these different components of the mixed population.

Cell sorting according to the methods of the invention provides sufficient numbers of separated drug-sensitive and drug-resistant neoplastic cells to be able to perform gene expression analysis. Gene expression analysis is performed to detect differences in gene expression between pure populations of neoplastic cells that are sensitive to a cytotoxic, chemotherapeutic drug and drug resistant neoplastic cells. RNA from the drug resistant neoplastic cells and drug sensitive neoplastic cells separated, most preferably, by FACS sorting is individually isolated and cDNA prepared therefrom. In preferred embodiments, the cDNA is detectably labeled, for example using radioactively-labeled or fluorescently-labeled nucleotide triphosphates. Hybridization of gene expression microarrays produces pattern of gene expression specific for cytotoxic, chemotherapeutic drug resistant neoplastic cells and neoplastic cells sensitive to the same drug and derived from the same cytotoxic drug-treated mixed cell population from which the drug-resistant cells were obtained. Identification of genes and patterns of genes differentially expressed in these cells is established by comparison of the gene expression pattern obtained by performing the microarray hybridization analysis on cDNA from neoplastic cells that are resistant to and sensitive to the cytotoxic, chemotherapeutic drug. Gene expression patterns specific for different tumor types, neoplastic cells and cytotoxic, chemotherapeutic drugs are obtained using the inventive methods.

The following Examples are intended to further illustrate certain preferred embodiments of the invention and are not limiting in nature.

EXAMPLE 1
Tumor Specimen Handling

Viable tumors samples were obtained from patients with malignant disease and placed into Oncotech transport media (complete medium, RPMI supplemented with 3% Fetal Calf Serum and antibiotics, as described below in the section Tissue Culture and Expansion) by personnel at the referring institution immediately after collection and shipped to Oncotech by overnight courier for the purpose of determining the tumors in vitro drug response profile. Upon receipt, data on tissue diagnosis, treatment history, referring physician, and patient information about the specimen was entered into a computer database. The tumor was then processed by the laboratory where three areas of the tumor are removed from the sample, fixed in Formalin, paraffin embedded, sectioned and Hematoxylin and eosin stained for pathologists' review to ensure agreement with the referring institution histological diagnosis. After in vitro drug response of the tumor specimens were determined by the laboratory, this information was sent back to the treating physician to aid in their treatment selection.

The remainder of the sample is disaggregated mechanically and processed into a cell suspension for the Extreme Drug Resistance (EDR) assay. A cytospin preparation from a single cell suspension of the tumor was examined by a technologist to determine the presence and viability of malignant cells in the specimen.

EDR Assay

The EDR assay is an agarose-based culture system, using tritiated thymidine incorporation to define in vitro drug response. This assay is predictive of clinical response (Kern et al., 1990, "Highly specific prediction of antineoplastic resistance with an in vitro assay using suprapharmacologic drug exposures," *J Nat. Cancer Inst.* 82:582–588). Tumors were cut with scissors into pieces of 2 mm or smaller in a Petri dish containing 5 mL of complete medium. The resultant slurries were mixed with complete media containing 0.03% DNAase (2650 Kunitz units/mL) and 0.14% collagenase I (both enzymes obtained from Sigma Chemical Co., St. Louis, Mo.), placed into 50 ml Erlenmeyer flasks with stirring, and incubated for 90 min at 37° C. under a humidified 5% $CO_2$ atmosphere. After enzymatic dispersion into a near single cell suspension, tumor cells were filtered through nylon mesh, and washed in complete media. A portion of the cell suspension was used for cytospin slide preparation and stained with Wright-Giemsa for examination by a medical pathologist in parallel with Hematoxylin-Eosin stained tissue sections to confirm the diagnosis and to determine the tumor cell count and viability. Tumor cells were then suspended in soft agarose (0.13%) and plated at 20,000–50,000 cells per well onto an agarose underlayer (0.4%) in 24-well plates. Tumor cells were incubated under standard culture conditions for 4 days in the presence or absence of a cytotoxic concentration of a chemotherapeutic agent. Cells were pulsed with tritiated thymidine (New Life Science Products, Boston, Mass.) at 5 $\mu$Ci per well for the last 48 hours of the culture period. After labeling, cell culture plates were heated to 96° C. to liquify the agarose, and the cells are harvested with a micro-harvester (Brandel, Gaithersburg, Md.) onto glass fiber filters. The radioactivity trapped on the filters was counted with an LS-6500 scintillation Counter (Beckman, Fullerton, Calif.). Untreated cells served as a negative control. In the positive (background) control group, cells were treated with a supratoxic dose of Cisplatin (33 $\mu$M), which causes 100% cell death. Detectable radioactivity for this group was considered non-specific background related to debris trapping of tritiated thymidine on the filter. After subtracting background control values, percent control inhibition (PCI) of proliferation was determined by comparing thymidine incorporation by the treatment group with incorporation by the negative control group: PCI=100% ×[1–(CPM treatment group CPM control group)]. Determinations of drug effects on tumor proliferation was performed in duplicate or triplicate. Tumor cell lines tested in the EDR assay were handled in a fashion comparable to solid tumors and plated at 1,000–5000 cells per well. Cell lines were harvested with trypsin and washed twice in phosphate buffered saline (PBS) prior to their addition to the culture plates.

Tissue Culture and Cell Expansion

All cell lines were maintained in RPMI 1640 (GibcoBRL, Grand Island, N.Y.) supplemented with 10% fetal calf serum (FCS, Gemini Bioproducts, Inc., Calabasas, Calif.), 100 IU/ml penicillin, 100 mg/ml streptomycin, and 2 mM L-glutamine (all purchased from Irvine Scientific, Irvine, Calif.) (this mixture is termed "complete medium" herein). Cells were harvested with 0.25% trypsin (GibcoBRL) after washing twice with phosphate-buffered saline (PBS, Irvine Scientific), then washed with complete medium, counted and checked for viability using trypan blue or propidium iodide (PI)-based flow cytometry, and processed for flow cytometry analysis or sorting.

In order to provide sorted tumor cells with optimal growth conditions, Becton Dickinson BIOCOAT microenvironment cell culture system was used. Tissue culture flasks (T-25, T-75, T-175, and T-225, Becton Dickinson, San Jose, Calif.) coated with rat-tail collagen I as a substrate for adhesion and growth of neoplastic cells were used in all experiments to expand sorted populations for gene array and cell sorting studies.

To approximate in vitro conditions for the growth neoplastic cells to the in vivo growth environment, Ultra Low Attachment 24-well plates (Costar, N.Y.) comprised of a covalently bound hydrogel layer that is hydrophobic and neutrally charged. This hydrogel surface inhibited non-specific immobilization of anchorage-dependent neoplastic cells via hydrophobic and ionic interactions and created an in vitro environment for culturing sorted and expanded neoplastic cells in organoid cultures. In titration experiments, the SKBR3 cell line (human breast cancer cell line, obtained from the American Type Culture Collection, Manassas, Va.) was plated in 24-well cytophobic plates at 500,000 cells per well, in duplicate, and treated with doxorubicin at concentrations of 0.02 $\mu$M, 0.04 $\mu$M, 0.08 $\mu$M, 0.17 $\mu$M, and 0.34 $\mu$M in complete medium for 5 days. As with the EDR assay described above, cells were pulsed with tritiated thymidine at 5 $\mu$Ci per well for the last 48 hours of the culture period and harvested with a micro-harvester. PCI was determined by comparing thymidine incorporation by the treatment group with incorporation by the negative control group (see section "EDR Assay"). Essentially the same experimental design was utilized to evaluate doxorubicin resistance of a fresh breast carcinoma sample # 80060899, using doxorubicin concentrations as follows: 0.001 $\mu$M, 0.0025 $\mu$M, 0.005 $\mu$M, 0.01 $\mu$M, 0.02 $\mu$M, 0.04 $\mu$M, 0.085 $\mu$M, and 0.17 $\mu$M.

To assess apoptotic potential of the SKBR3 cell line, SKBR3 cells at 500,000 per well were treated with doxorubicin at a pre-determined $IC_{50}$ (0.04 $\mu$M) and $IC_{90}$ (0.34 $\mu$M) concentrations for 24 and 48 hr, and analyzed by flow cytometry for Annexin V binding. In sorting experiments involving the SKBR3 cell line or sorted and expanded tumor populations, $3-5 \times 10^7$ cells were plated in cytophobic 24-well plates at 500,000 cell per well, exposed to doxorubicin for 24 hours, collected by pipetting, washed with PBS with 1% FCS, and sorted on the basis of Annexin V binding.

Flow Cytometry Analysis and Cell Sorting

Samples of viable neoplastic cells were immediately analyzed on Becton Dickinson FACSort or FACSVantage flow cytometers equipped with a Coherent Enterprise laser tuned to 488 nm. Forward scatter, side scatter, FL-1 (FITC, fluorescein isothiocyanate), FL-2 (PE, phycoerythrin), and FL-3 (PI, propidium iodide) parameter data were collected in list mode. 10,000 events per sample were collected and consequently analyzed using the Becton Dickinson CellQuest flow cytometry acquisition software. In all samples, PI was added to exclude dead cells. Data shown are PI negative (viable) cells.

Flow sorting was performed on the Becton Dickinson FACSVantage instrument using the following parameters. In surface tumor-specific marker-based flow sorting, neoplastic cells numbers and viability were determined using the FACScan. Cells were the washed in 45 ml of serum-free RPMI and centrifuiged at 1572 g (4° C., 5 min). An aliquot (0.5–1×10$^6$ cells) was labeled by the isotype control preparation (mouse IgGI from Sigma, at a final concentration of 2 $\mu$g/mL) at 4° C. for 30 min. The remaining cells were labeled under the same conditions with the 9GG.10 anti-human HER2 monoclonal antibody (mAb) at 2 $\mu$g/mL (Neomarkers, Fremont, Calif.) or the 111.6 anti-human EGF-R mAB (Neomarkers). Cells were washed twice by ice-cold serum-free RPMI and centrifuged at 1572×g (4° C., 5min). Washed cells were then labeled on ice with phycoerythrin (PE)-labeled anti-mouse IgG1 for 30 min, washed again in ice-cold PBS +1% FCS (1572×g, 4° C., 5 min), re-suspended in cold PBS+1%FBS supplemented with PI (1 $\mu$g/mL), and sorted on the FACSVantage. Sorted neoplastic wells were collected in a 5 mL plastic tube containing 2 mL of a 50/50 mixture of serum-free RPMI and FCS. Cell counts were recorded from the FACSVantage. After one wash with cold PBS (centrifugation at 1572×g, 4° C., 5 min), cell numbers and viabilities were determined using the FACScan. Cell pellets were used for RNA extraction if at least $2 \times 10^6$ viable sorted HER2$^+$ or EGFR$^+$ cells were recovered. An additional aliquot of $5 \times 10^5$ cells were expanded for further analysis. If less than $2.5 \times 10^6$ viable sorted cells were recovered, all sorted cells were cultured in vitro for further analysis. Purity (defined as the percentage of neoplastic cells in the sample) and viability of the sorted populations were determined using the FACSVantage.

Flow sorting based on Annexin V binding was performed using the same protocol and FITC-labeled Annexin V (PharMingen, San Diego, Calif.), with the following modifications. The following controls were used to set up compensation and quadrants: (1) unstained cells (autofluorescence control), (2) cells stained with Annexin V-FITC only (no PI), and (3) cells stained with PI only (no Annexin V-FITC). Washed neoplastic cells were mixed with Annexin V-FITC (5 $\mu$L of the probe per $1 \times 10^5$ cells) and/or PI (10 $\mu$L of 50 $\mu$g/mL stock solution per $1 \times 10^5$ cells), gently vortexed and incubated at room temperature (20–25° C.) in the dark for 15 min. Annexin V-labeled cells were then re-suspended in 1X binding buffer provided by PharMingen and sorted on the FACSVantage, as recommended by the manufacturer. The following cell populations are separated: Annexin V+/PI-(sensitive cells) and Annexin V-/PI-(resistant cells). Sorted cells were collected in a FACS tubes, and purity and viability of the sorted populations were determined using the FACSVantage as described above.

SKBR3 Cells

Results of cell sorting experiments as described above with human breast carcinoma cell line SKBR3 are shown in FIGS. 2 through 6.

Figure 2A:
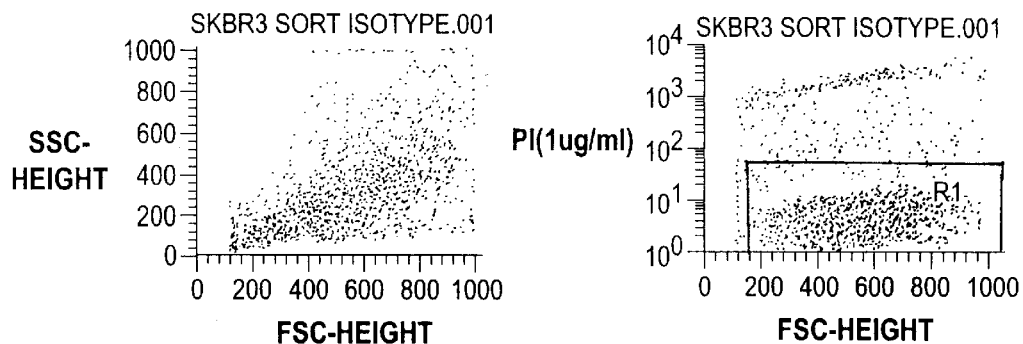
FIGS. 2A through 2C are fluorescence-activated cell sorting (FACS) profiles of SKBR3 cells showing cell scatter (FIG. 2A, left), cell viability (FIG. 2A, right), HER2 antibody binding versus non-specific isotypic antibody binding (FIG. 2B), and a resort of HER2 antibody binding cells sorted as shown in FIG. 2B (FIG. 2C).
Figure 2B:
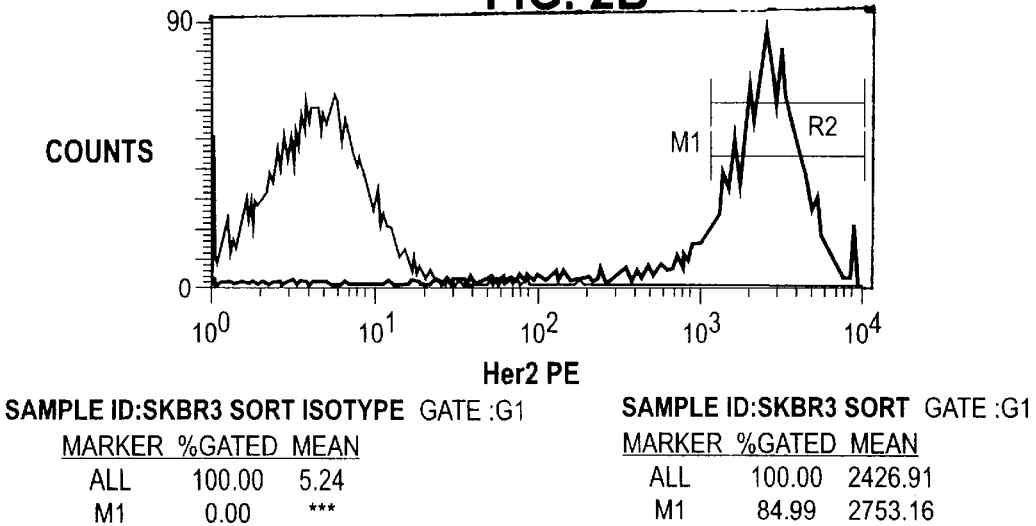
Figure 2C:
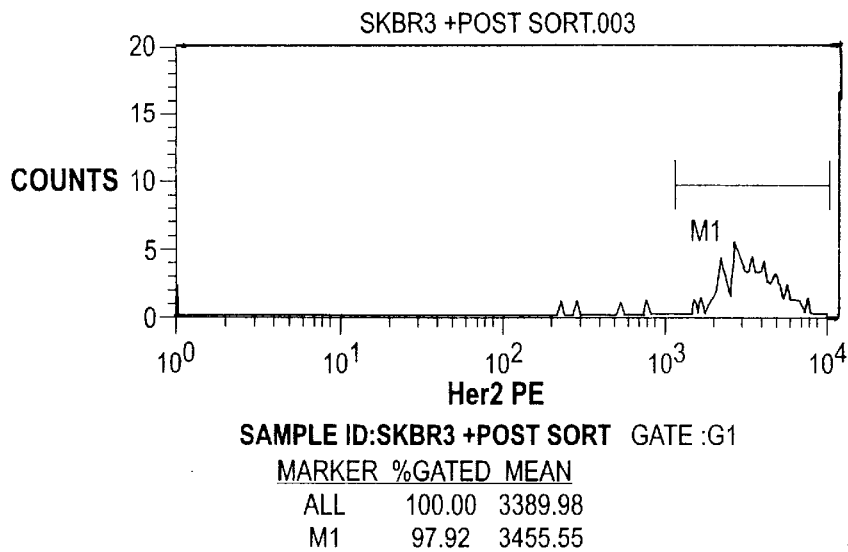
Figure 6A:
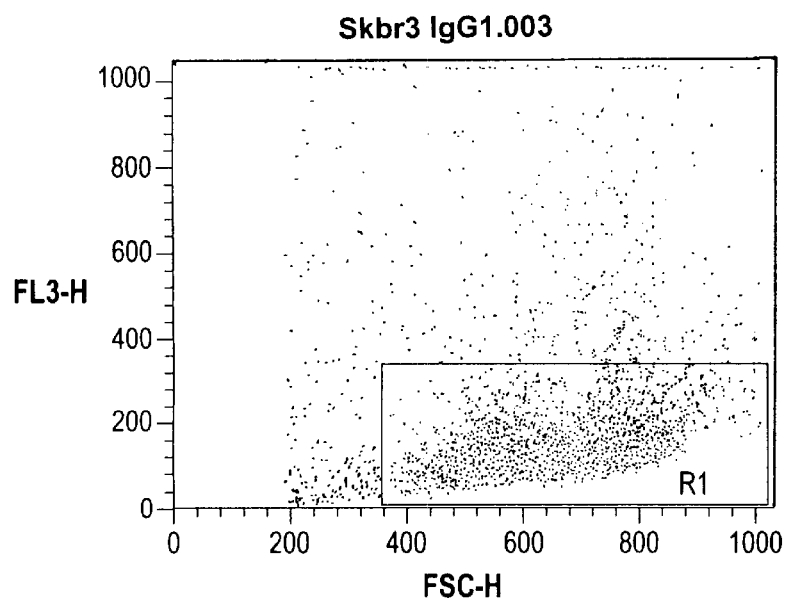
FIGS. 6A and 6B are FACS profiles of HER2 antibody binding to SHBR3 cells analyzed after cell culture following separation from non-neoplastic cells by FACS based on anti-HER2 antibody binding.
Figure 6B:
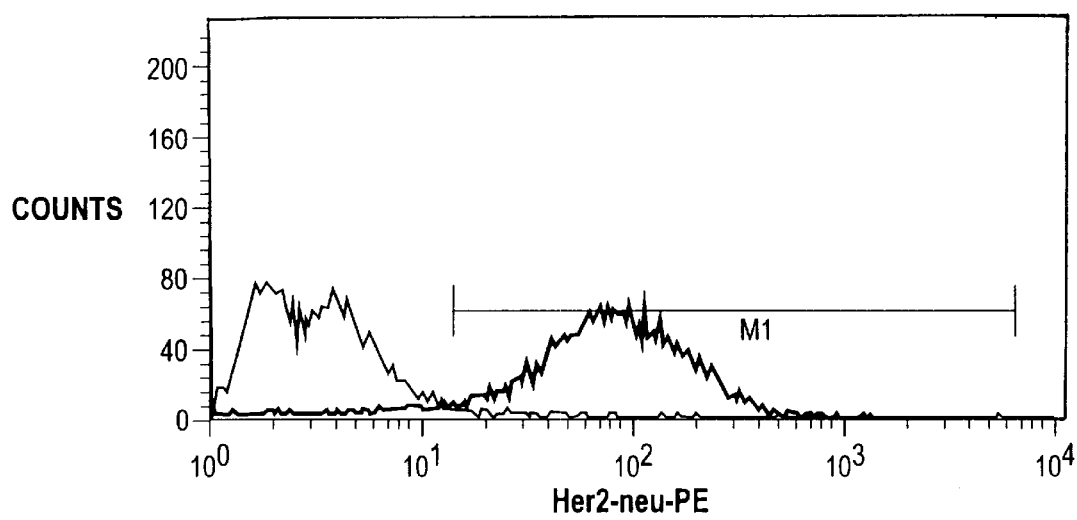

Cell sorting of SKBR3 cells is shown in FIGS. 2A through 2C. FIG. 2A (left) show that, even for a cultured cell line there is a wide size and shape distribution, as evidenced by the scattering in the upper right hand quadrant above the clustered scattering of the main cell mass. Staining with propidium iodide followed by sorting (FIG. 2A, right) illustrates that a certain proportion of the cells are dead or dying and unable to exclude the fluorescent vital stain (the scattering above the line in the lower righthand quadrant. Staining with phycoerythrin-conjugated HER2 monoclonal antibody is shown in FIG. 2B. The thicker-lined scatter trace illustrates specific binding, and the thinner-lined trace illustrates non-specific binding of an antibody isotype control. Notice that there is considerable HER2 antibody-associated fluorescence (about 15%) in at intensities between 0 and 102. This indicates that HER2 expression in this cell line is heterogeneous. That these results indicate true cellular heterogeneity is shown by comparison to FIG. 2C, which is a HER2 antibody stained resort of the population represented by M1 in the graph shown in FIG. 2B. There is substantially no HER2-associated fluorescence in the range of 0 and 102, indicating that the sorted population is much more homogenous in HER2 expression than the original unsorted cell line. FIGS. 6A and 6B show that this population is maintained after returning to cell culture after sorting. FIG. 6A shows that the majority of the cells remained viable, and FIG. 6B shows that the cells bound HER2 (although a certain amount of heterogeneity can be seen to be developing in the population).

Figure 3:
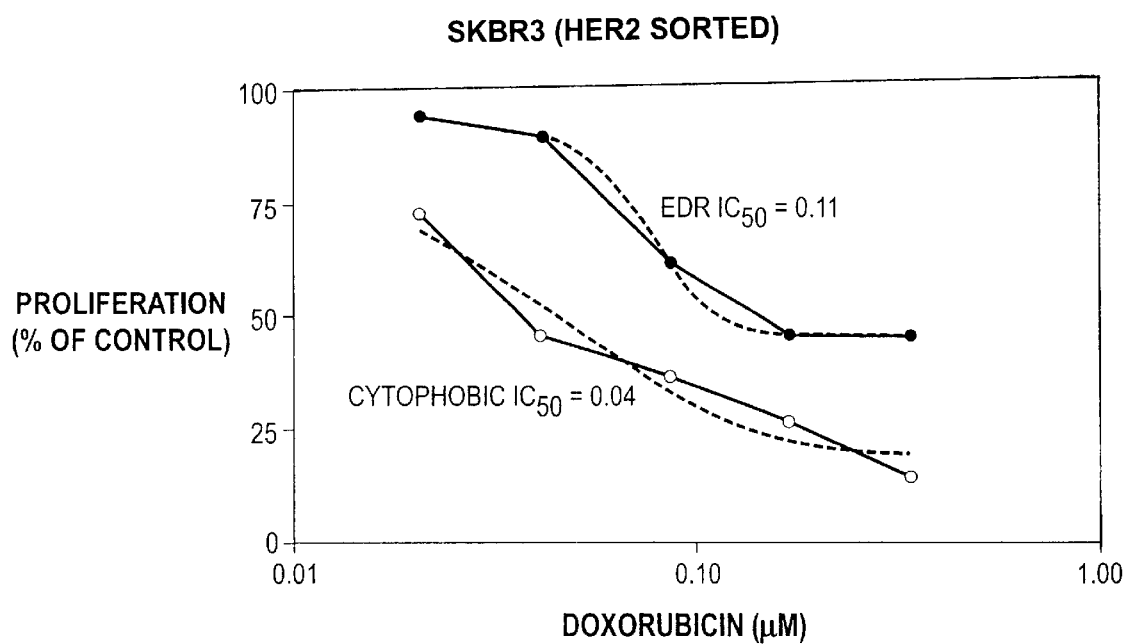
FIG. 3 is a graph showing drug sensitivity in a HER2-sorted population of SKBR3 cells as determined by EDR assay and cytophobic culture plate assay.

FIG. 3 shows a comparison of doxorubicin sensitivity in a HER2-sorted SKBR3 cell population such as the one shown in FIG. 2C as determined by EDR assay and cytophobic culture plate assay. Although the absolute $IC_{50}$ values differ, due to inherent differences in the techniques, the shape of the drug sensitivity curves are substantially parallel, indicating that cells exposed to cytotoxic drugs using the cytophobic plate assay are equivalent to cells assayed using the EDR assay. This is important because cells assayed by the EDR assay are unsuitable for RNA isolation and gene expression analyses.

Figure 5A:
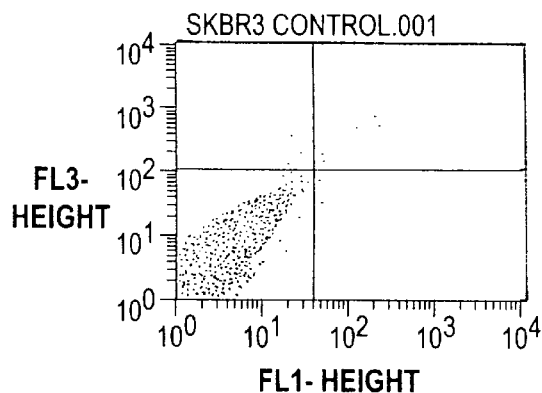
FIGS. 5A through 5D are fluorescence-activated cell sorting (FACS) profiles of cells from SKBR3 cells after in vitro cytotoxic drug treatment.
Figure 5B:
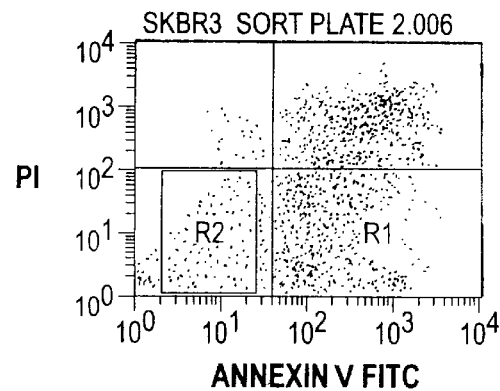
Figure 5C:
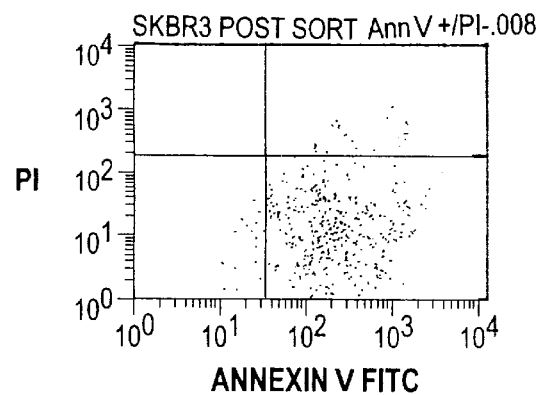
Figure 5D:
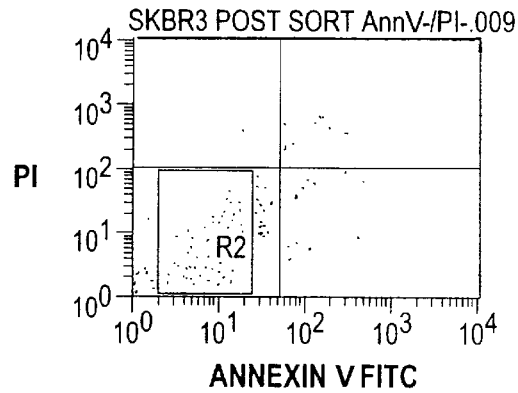

SKBR3 cells treated with cytotoxic drugs were sorted after treatment with the apoptosis-discriminating agent Annexin V to separate living, drug resistant cells from apoptotic, drug sensitive cells. These results are shown in FIGS. 5A through 5D. FIG. 5A shows cell scatter of the mixed population concentrated in the lower left quadrant, indicating that the population was relatively homogenous. The results of sorting after propidium iodide staining and Annexin V treatment, followed by immunochemical staining with an FITC-conjugated anti-annexin V antibody is shown in FIG. 5B. This sort resulted in separation into living, drug-resistant neoplastic cells (R2 in the lower left quadrant), apoptotic, drug-sensitive cells (R1 in the lower right quadrant) and dying, drug-sensitive cells (in the upper right quadrant). Cell populations isolated from R1 (FIG. 5C; drug-sensitive cells) and R2 (FIG. 5D; drug-resistant cells) provides confirmation that the mixed cell population was separated into two distinct subpopulations based on binding of the fluorescently-labeled anti-Annexin V reagent.

Figure 4:
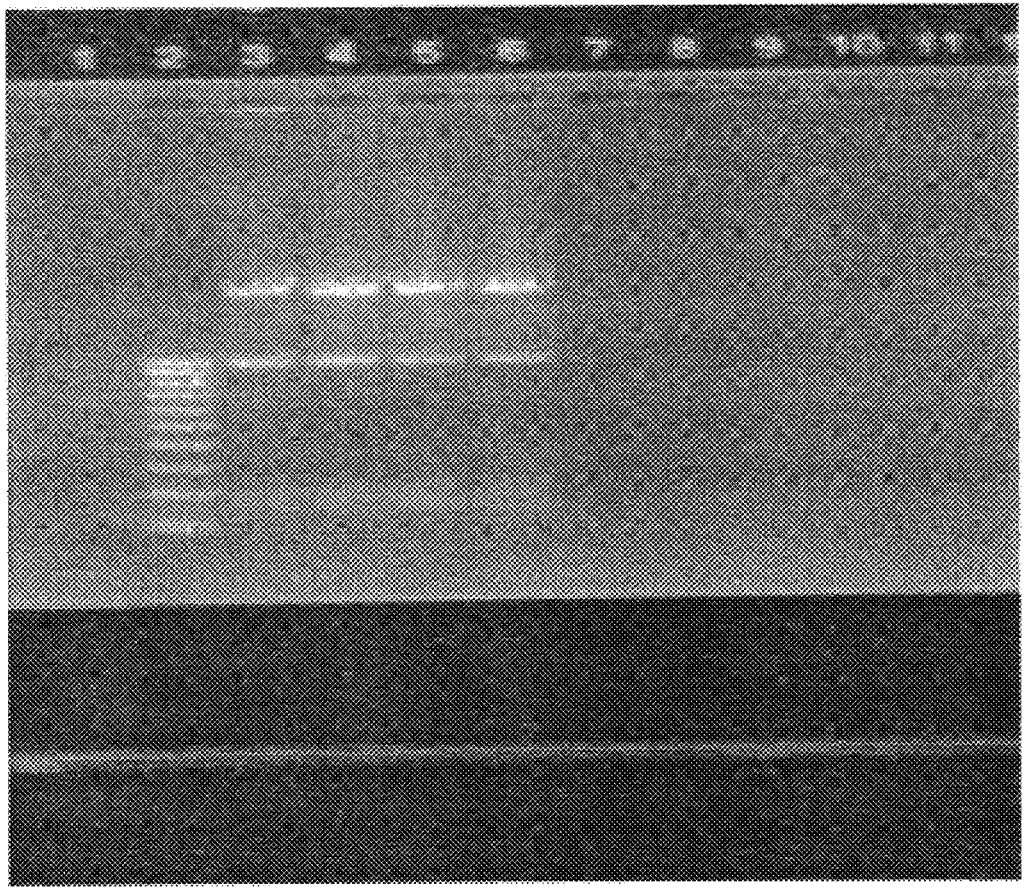
FIG. 4 is a photograph of an agarose gel electrophoretic analysis of RNA integrity from cytotoxic drug-treated cells. Lane 1 is a blank control; lane 2 is a 100 nucleotide control; lane 3 is RNA from doxorubicin-resistant SKBR3 cells; lane 4 is RNA from doxorubicin-sensitive SKBR3 cells; lane 5 is RNA from doxorubicin-resistant cells; and lane 6 is RNA from doxorubicin-sensitive cells from a human breast tumor sample.

RNA was isolated from these cell populations and analyzed. FIG. 4 is a photograph of an agarose gel electrophoretic analysis of RNA isolated from sorted, cytotoxic drug-treated cells. Lane 1 is a blank control; lane 2 is a 100 nucleotide size marker; lane 3 is RNA from doxorubicin-resistant SKBR3 cells and lane 4 is RNA from doxorubicin-sensitive SKBR3 cells, each population sorted as described. These results indicate that the RNA obtained from both drug sensitive and drug resistant cells has retained its molecular integrity (since the ribosomal RNA bands show essentially equal staining intensity.

These results demonstrate that the cell sorting methods disclosed herein are capable of providing cellular RNA from a mixed population of a tumor cell line into s separated population of drug resistance and drug sensitive cells.

Human Breast Carcinoma Tumor Sample

Results of cell sorting experiments as described above with disaggregated cells from a human breast carcinoma tumor sample are shown in FIGS. 10 through 12.

FACS sorting of disaggregated cells from a human breast carcinoma tumor sample is shown in FIGS. 10A through 10D. FACS analysis after propidium iodide staining is shown in FIG. 10A, where about 83% of the cells were viable. FIG. 10B shows negligible non-specific isotypic antibody binding after staining of the viable cells with phycoerythrin-conjugated mouse $Ig_2G1$ antibody. FIG. 10C shows separation of the population into apoptotic, drug-sensitive neoplastic cells (R2, about 69%) and living, drug-resistant neoplastic cells (R3, about 6.5%). FIG. 10D provides confirmation that 96% of the sorted cells are viable (FIG. 10D, top) and that 97% of the sorted cells were HER2 positive (FIG. 10D, bottom).

Figure 11A:
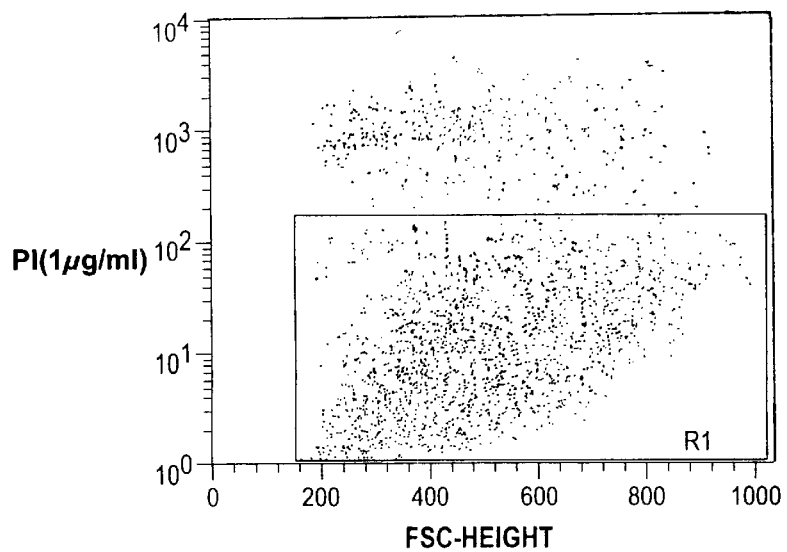
FIGS. 11A and 11B are FACS profiles of HER2 antibody binding human breast tumor cells analyzed after cell culture following separation from non-neoplastic cells by FACS based on anti-HER2 antibody binding.
Figure 11B:
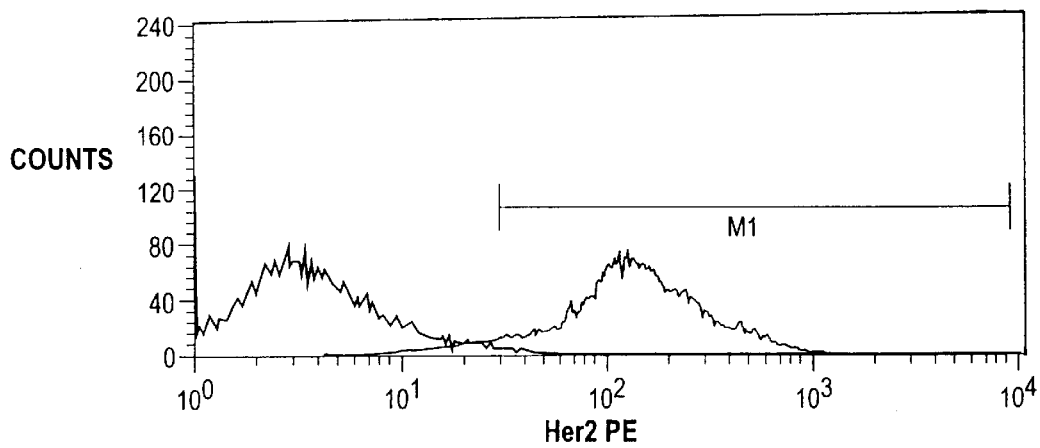

FIGS. 11A and 11B shows HER2 antibody binding in these human breast tumor cells analyzed after cell culture following separation from non-neoplastic cells by FACS based on anti-HER2 antibody binding. FIG. 11A shows that 91.5% of the cells remained viable, and FIG. 11B shows that 96.2% of the cells bound HER2.

Figure 12A:
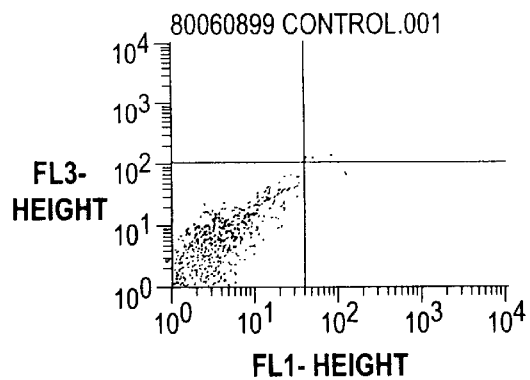
FIGS. 12A through 12D are fluorescence-activated cell sorting (FACS) profiles of cells from a human breast tumor sample after in vitro cytotoxic drug treatment.
Figure 12B:
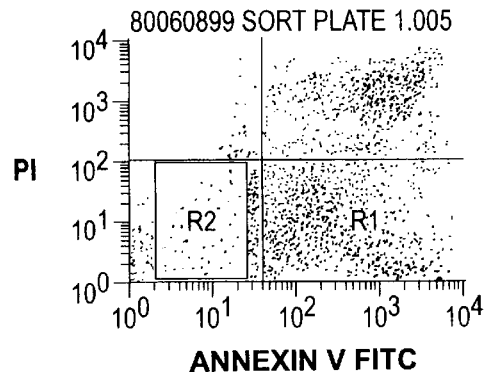
Figure 12C:
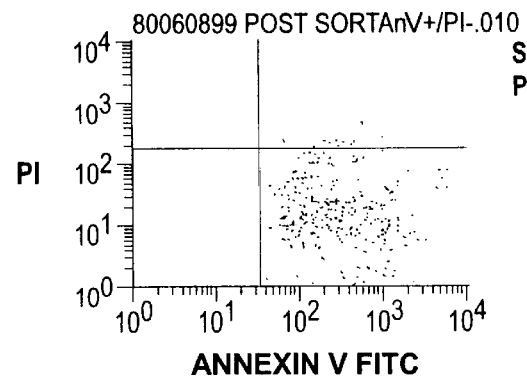
Figure 12D:
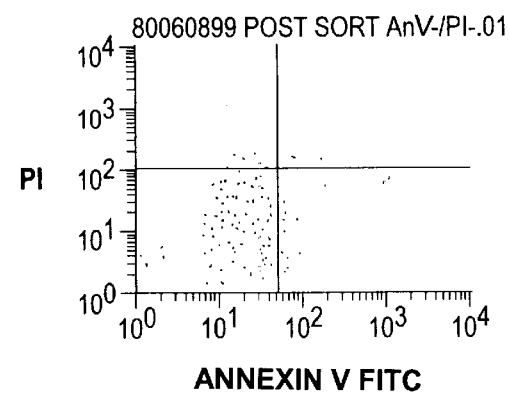

Viable neoplastic human breast carcinoma cells were separated as described above from the disaggregated tumor sample and treated with cytotoxic drugs. These cells were then sorted after treatment with the apoptosis-discriminating agent Annexin V to separate living, drug resistant cells from apoptotic, drug sensitive cells. These results are shown in FIGS. 12A through 12D. FIG. 12A shows cell scatter (99.8% in the lower left quadrant), indicating that the cells formed a relatively homogenous population in terms of cell size and shape. FIG. 12B shows separation of this population into living, drug-resistant neoplastic cells (R2; 14.6% of cells in the lower left quadrant), apoptotic, drug-sensitive cells (R1; 40.5% in the lower right quadrant) and dying, drug-sensitive cells (44.7% in the upper right quadrant). Confirmation that these cells had been sorted into distinct populations based on drug sensitivity or resistance is show in FIGS. 12C and 12D. FIG. 12C shows that apoptotic, drug-sensitive cells (93.3% of the sorted cells) resort into the lower right quadrant). FIG. 12D shows that living, drug-resistant cells (92.25% of the sorted cells) resort into the lower left quadrant).

Analysis of RNA isolated from these cell populations is shown in FIG. 4. Lane 5 shows RNA from FACS sorted doxorubicin-resistant human breast carcinoma cells, and lane 6 shows RNA from FACS sorted doxorubicin-sensitive human breast carcinoma cells, each population sorted as described. These results indicate that the RNA obtained from both drug sensitive and drug resistant cells isolated from a human breast carcinoma has retained its molecular integrity (since the ribosomal RNA bands show essentially equal staining intensity).

EXAMPLE 2

Gene Array Analyses

Cultured cells, or neoplastic cells prepared by FACS sorting as described in Example 1, were used to make mRNA for performing gene array hybridization analyses.

mRNA differential display is an effective method for isolating genes that are expressed differentially among different tissues. High-density cDNA arrays are a valuable tool for the simultaneous analysis of differential gene expression. The use of flow cytometry for the separation of pure populations of cells from complex heterogeneous tissue and high-density microarray technology provides a unique opportunity to perform high-throughput genetic analysis of pure populations of malignant cells. To demonstrate the feasibility of integrating and applying these technologies to clinical specimen, we examined the differential gene expression between pre-sorted, mixed, and post-sorted MCF7 (human breast carcinoma cells) and HUVEC (human endothelial cells) cell lines.

The gene expression profile of at least four thousand genes can be successfully generated using non-amplified RNA derived from distinct cell populations within mixed populations of cells. These results indicate that high-throughput gene expression analysis can be achieved after flow sorting for the pure population of cells and should be of value in elucidating the genetic events associated with cellular sub-populations within neoplastic tissue.

RNA Isolation

Cells were collected by gentle centrifugation (about 1500×g) to preserve their integrity. After isolating the pelleted cells from the supernatant fluid, the cells were lysed in TRIzol® Reagent (Life Technologies™, Rockville, Md.) by repetitive pipetting, using about 1 mL of Trizol reagent per $1$–$10 \times 10^6$ cells. The lysed cell sample was then incubated for 5 minutes at room temperature to permit the complete dissociation of nucleoprotein complexes. To this mixture was added about 0.2 mL chloroform per 1 mL of Trizol Reagent and the tube shaken vigorously and then incubated at room temperature for 2 minutes. The organic and aqueous phases were separated by centrifugation at about 12,000×g for 15 minutes at 5° C. The aqueous phase was carefully collected and transferred to a fresh tube, and the RNA precipitated by mixing with mixing with 0.5 mL of isopropyl alcohol. The samples were then incubated at room temperature for 10 minutes and centrifuged at 12,000×g for 10 minutes at 5° C. The supernatant was carefully removed from the RNA pellet, which was then washed once with 1 mL of 75% ethanol. The ethanol was removed and the RNA pellet air-dried for 10 minutes. Finally, the RNA pellet was dissolved in RNase-free water by incubating for 10 minutes at 55° C.

The yield and purity of total RNA was determined spectrophotometrically. The integrity of the purified RNA was determined by agarose gel electrophoresis using conventional methods.

MicroArray Assay cDNA Probe Preparation cDNA was prepared from cellular RNA as follows, 2.5 μg of cellular RNA was mixed with 2.0 μL Oligo dT (1 μg/μL 10–20 mer mixture) in a total volume of 10.0 μL and then placed at 70° C. for 10 minutes followed by brief chilling on ice for 2 minutes. To this mixture was added 6.0 μL 5X First Strand Buffer, 1.0 μL DTT (0.1 M), 1.5 μL dNTP mixture containing dATP, dGTP, and dTTP a;plo;'/ta concentration of 20 mM, 1.5 μL Reverse Transcriptase (Superscript II, RNase H⁻, Life Technologies, Rockville, Md.) and 10 μL $\alpha(^{33}P)$-dCTP (10 mCi/mL with a specific activity of 3000 Ci/mmol), in a total volume of 30 μL. $^{33}$P-labeled dCTP is used because the beta-particle emission energy of this isotope is about 15% of the beta-particle energy of the more commonly-used $^{33}$P radioisotope. This reduces the amount of "spill-over" radioactive emission between closely-spaced sites on the microarray, and makes detecting positive hybridization easier and more reliable. This reaction mixture was incubated for 90 minutes at 37° C. The reaction mixture was diluted to a final volume of 100 μL with water, and the entire volume loaded on a Bio-Spin 6 chromatography column (BioRad, Hercules, Calif.). cDNA was purified from unincorporated nucleotides following the manufacturer's instructions. The efficiency of cDNA synthesis was calculated based on the radioactivity of the probe, and was generally between 10–15%. The entire probe mixture was used for hybridization.

Hybridization

Microarrays (Known Gene Array) were obtained from Research Genetics (Huntsville, Ala.).

Prior to using new membranes, the membranes were washed for at least 5 minutes with gentle agitation in a boiling (95–100° C.) solution of 0.5% SDS. The arrays were prehybridized prior to use in hybridization roller bottles containing 5 mL MicroHyb hybridization solution. Blocking reagents, including 5.0 μg human Cot-1 DNA and 5.0 μg poly dA were added to the prehybridization mixture (wherein the Cot-1 DNA is first denatured by boiling for 3 minutes). Prehybridization was performed by incubating the membrane in prehybridization buffer at 42° C. for 4 to 6 hours.

Hybridization of radiolabeled cDNA prepared as described above to the prehybridized microarrays was performed as follows. The radiolabeled cDNA probe was denatured by boiling for 3 minutes and then rapidly chilled on ice for 2 minutes. The probe was introduced into the hybridization roller bottle containing the membrane and the prehybridization mixture. The membrane was hybridized to the probe by incubation overnight (12–18 hours) at 42° C. in a hybridization roller oven at 8–10 rpm. After the hybridization reaction was complete, the membranes were washed twice with 30 mL of 2×SSC containing 1% SDS at 50° C. for 20 minutes in hybridization oven at 12–15 rpm. The membranes were then washed in 1 OOmL of a solution of 0.5×SSC containing 1% SDS at room temperature for 15 minutes with gentle shaking. The washed membrane was then placed on a moist filter paper and wrap it with plastic wrap.

Hybridization was detected using a using a Cyclone phosphor imaging analyzer (Packard, Meriden, Conn.) by placing the hybridized membrane adjacent to the phosphor imaging screen. The membrane was exposed to the screen for a time sufficient to detect hybridization, following the manufacturer's instructions. Results were interpreted using Pathways™ software for analysis.

After exposure and data collection, the membranes were recovered for additional rounds of hybridization by stripping the hybridized radioactive probe. This was accomplished by washing the membranes in 500 mL of boiling solution of 0.5% SDS for 1 hour with vigorous shaking. The stripped membranes were stored moist at 4° C. until use.

Figure 7:
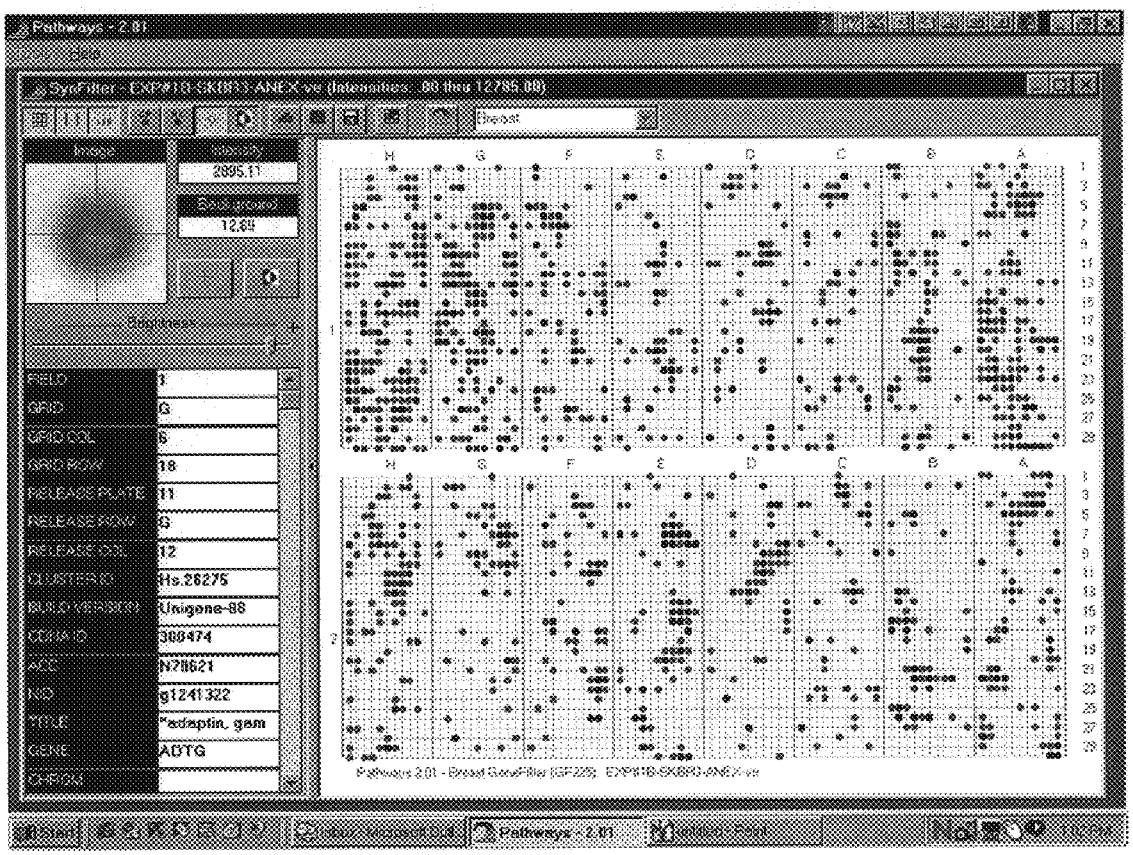
FIG. 7 is a schematic diagram of the results of a gene expression microarray analysis hybridized with cDNA prepared from doxorubicin-resistant SKBR3 cells.
Figure 8:
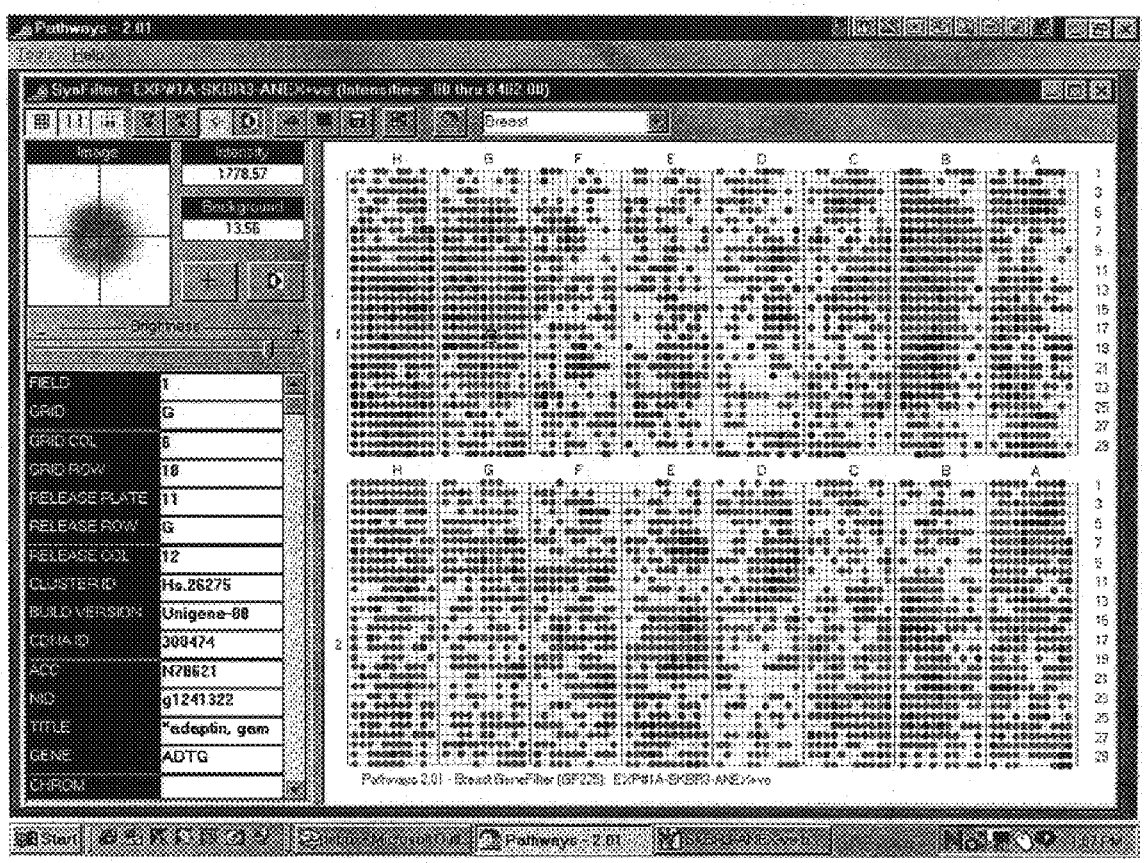
FIG. 8 is a schematic diagram of the results of a gene expression microarray analysis hybridized with cDNA prepared from doxorubicin-sensitive SKBR3 cells.
Figure 9:
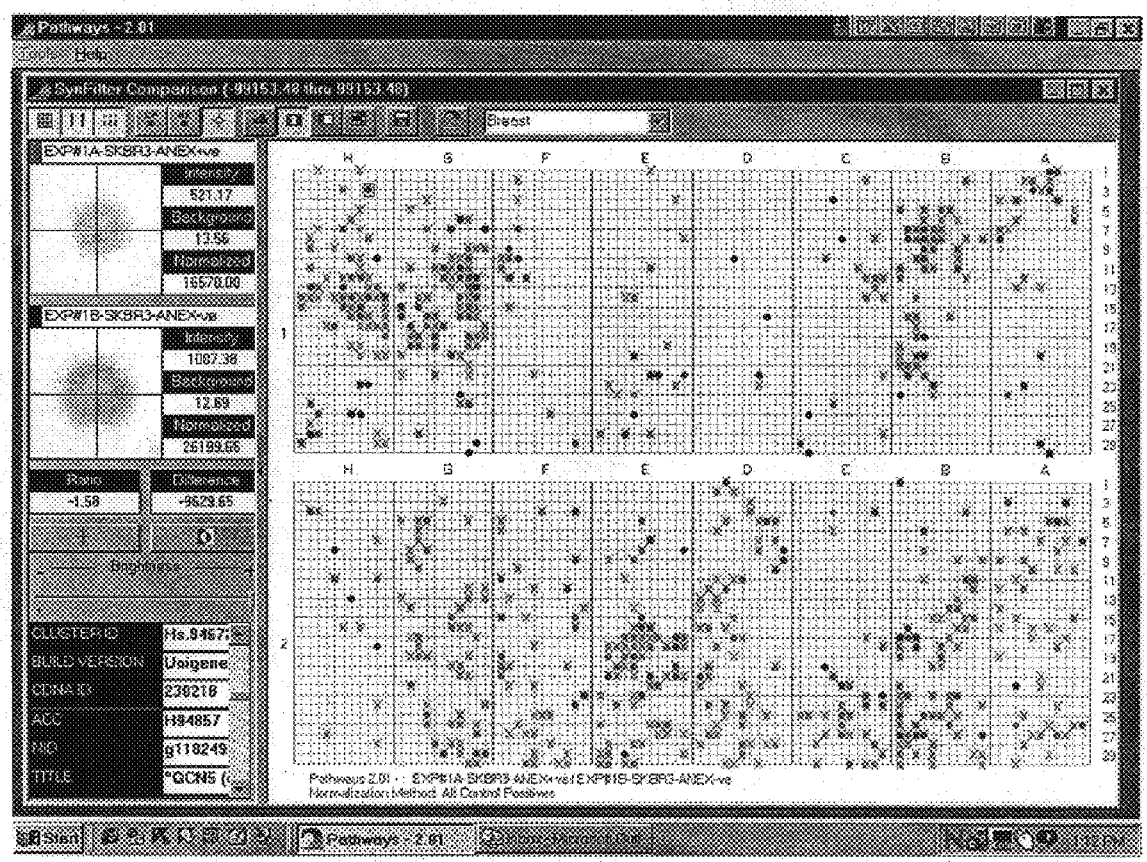
FIG. 9 is a schematic diagram of a comparison of the results of a gene expression microarray analysis hybridized with cDNA prepared from doxorubicin-sensitive SKBR3 cells with a gene expression microarray analysis hybridized with cDNA prepared from doxorubicin-sensitive SKBR3 cells.
Figure 13:
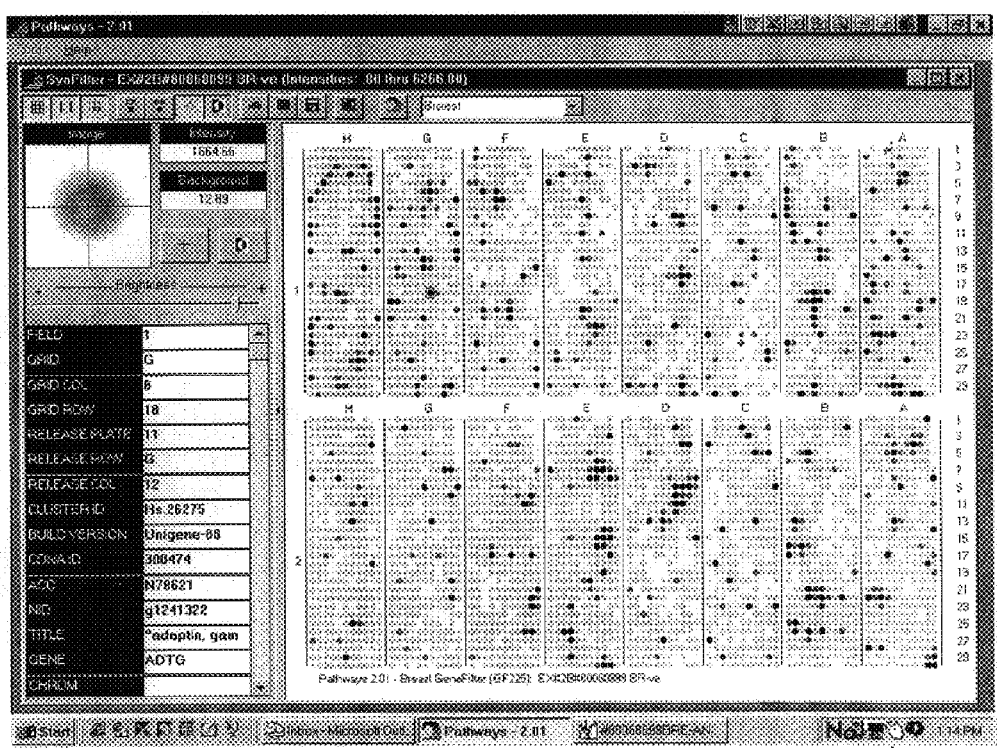
FIG. 13 is a schematic diagram of the results of a gene expression microarray analysis hybridized with cDNA prepared from doxorubicin-resistant human breast tumor-derived neoplastic cells.
Figure 14:
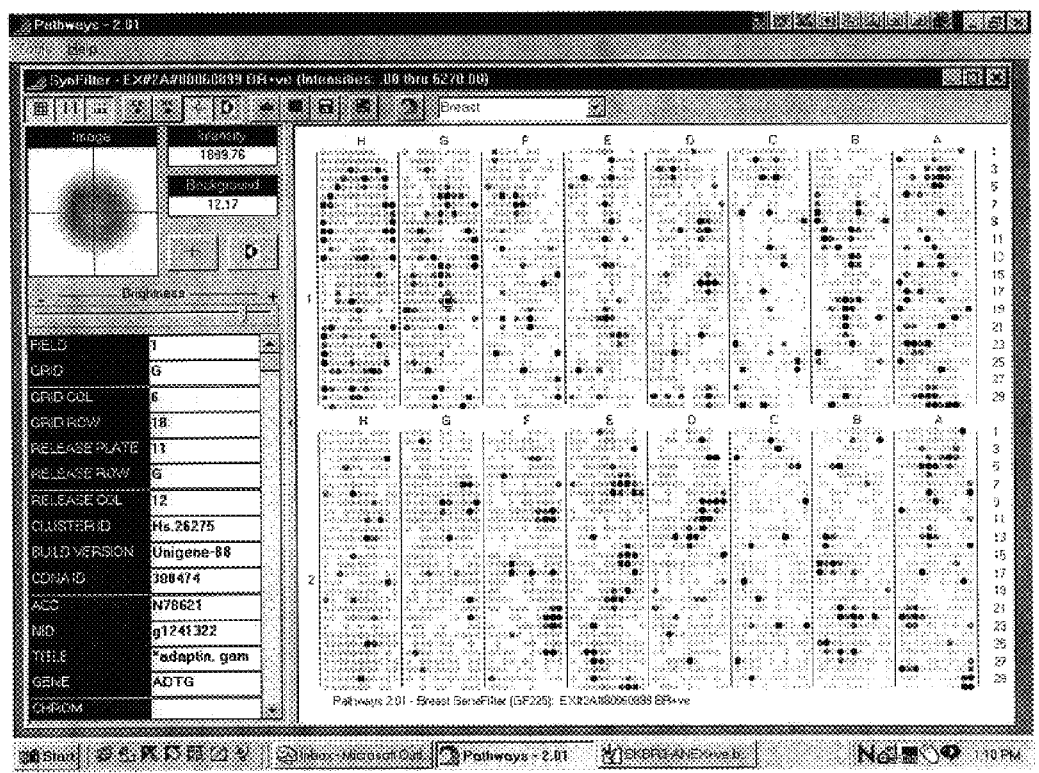
FIG. 14 is a schematic diagram of the results of a gene expression microarray analysis hybridized with cDNA prepared from doxorubicin-sensitive human breast tumor-derived neoplastic cells.
Figure 15:
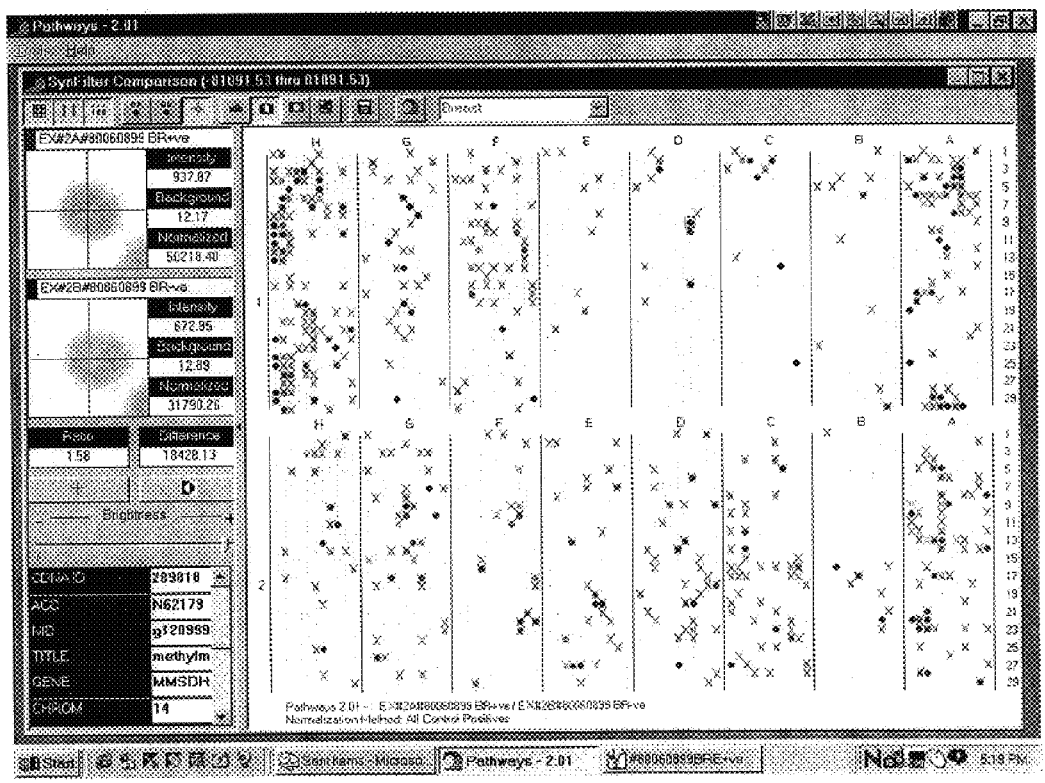
FIG. 15 is a schematic diagram of a comparison of the results of a gene expression microarray analysis hybridized with cDNA prepared from doxorubicin-sensitive human breast tumor-derived neoplastic cells with a gene expression microarray analysis hybridized with cDNA prepared from doxorubicin-sensitive human breast tumor-derived neoplastic cells.

Hybridization experiments as described herein were performed using cDNA prepared from FACS sorted populations of drug sensitive and drug resistant SKBR3 cells and human breast carcinoma cells as described in Example 1. Results of these assays are shown in FIGS. 7, 8 and 9 and Table I for SKBR3 cells and in FIGS. 13, 14 and 15 and Table II for human breast carcinoma cells. In the SKBR3 experiments, 40 genes were found to have significantly altered levels of expression (defined as a difference greater than or equal to 1.5 fold). These genes are identified in Table I. For the human breast carcinoma cell experiments, 63 genes were found to have significantly altered levels of expression (defined as a difference greater than or equal to 1.5 fold). These genes are identified in Table II.

It should be understood that the foregoing disclosure emphasizes certain specific embodiments of the invention and that all modifications or alternatives equivalent thereto are within the spirit and scope of the invention as set forth in the appended claims.

TABLE 1

SKBR3 Anexve–veSynFilComplR1.5.B&W.xls
Comparative differential gene expression analysis of SKBR3- Annexin positive (SKBR3-ANEX+ve) cells
versus SKBR3- Annexin negative (SKBR3-ANEX–ve) cells revealed that 40 genes had
significantly altered leveles of expression by 1.5-fold or greater. Of these 14 & 26 genes were found to be
differentially expressed in the SKBR3- Annexin positive and SKBR3- Annexin negative cells, respectively.

| FilterType GF 225 | Head1_BGAvg SKBR3-ANEX+ve | Head2_BGAvg SKBR3-ANEX–ve | Data1_RawIntensity SKBR3-ANEX+ve | Data2_RawIntensity SKBR3-ANEX–ve | field | grid | col | row | cluster id |
|---|---|---|---|---|---|---|---|---|---|
| Breast GeneFilter | 13.56254 | 12.69236 | 68.75561 | 35.91195 | 1 | A | 6 | 1 | Hs.11538 |
| Breast GeneFilter | 13.56254 | 12.69236 | 129.3607 | 77.66888 | 1 | A | 8 | 3 | Hs.19154 |
| Breast GeneFilter | 13.56254 | 12.69236 | 151.8963 | 65.16193 | 1 | B | 9 | 18 | Hs.182255 |
| Breast GeneFilter | 13.56254 | 12.69236 | 827.0767 | 1177.369 | 1 | B | 12 | 24 | Hs.81234 |
| Breast GeneFilter | 13.56254 | 12.69236 | 3348.075 | 4251.094 | 1 | C | 8 | 4 | Hs.214198 |
| Breast GeneFilter | 13.56254 | 12.69236 | 92.98527 | 134.1836 | 1 | C | 7 | 8 | Hs.25497 |
| Breast GeneFilter | 13.56254 | 12.69236 | 66.49899 | 87.71584 | 1 | C | 11 | 26 | Hs.20644 |
| Breast GeneFilter | 13.56254 | 12.69236 | 677.8284 | 828.687 | 1 | C | 11 | 30 | Hs.82045 |
| Breast GeneFilter | 13.56254 | 12.69236 | 124.8971 | 187.9308 | 1 | D | 8 | 10 | Hs.22405 |
| Breast GeneFilter | 13.56254 | 12.69236 | 3673.551 | 5320.43 | 1 | D | 4 | 16 | Hs.77550 |
| Breast GeneFilter | 13.56254 | 12.69236 | 86.78979 | 125.0546 | 1 | D | 5 | 22 | Hs.144700 |
| Breast GeneFilter | 13.56254 | 12.69236 | 48.40854 | 26.02505 | 1 | E | 2 | 22 | Hs.75879 |
| Breast GeneFilter | 13.56254 | 12.69236 | 2249.312 | 3584.547 | 1 | E | 5 | 22 | Hs.66576 |
| Breast GeneFilter | 13.56254 | 12.69236 | 54.74636 | 100.5361 | 1 | E | 8 | 26 | Hs.24301 |
| Breast GeneFilter | 13.56254 | 12.69236 | 133.5387 | 81.08858 | 1 | F | 11 | 9 | Hs.195453 |
| Breast GeneFilter | 13.56254 | 12.69236 | 91.99347 | 50.21226 | 1 | F | 10 | 10 | Hs.77273 |
| Breast GeneFilter | 13.56254 | 12.69236 | 307.1604 | 614.9251 | 1 | G | 2 | 7 | Hs.83422 |
| Breast GeneFilter | 13.56254 | 12.69236 | 126.5671 | 79.74345 | 1 | G | 5 | 24 | Hs.2384 |
| Breast GeneFilter | 13.56254 | 12.69236 | 70.14929 | 127.0265 | 1 | G | 3 | 29 | Hs.25180 |
| Breast GeneFilter | 13.56254 | 12.69236 | 166.2285 | 313.8372 | 1 | G | 4 | 30 | Hs.24297 |
| Breast GeneFilter | 13.56254 | 12.69236 | 521.1713 | 1007.375 | 1 | H | 4 | 3 | Hs.94672 |
| Breast GeneFilter | 13.56254 | 12.69236 | 117.3941 | 312.8566 | 1 | H | 3 | 10 | Hs.100560 |
| Breast GeneFilter | 13.56254 | 12.69236 | 722.8997 | 551.7939 | 1 | H | 7 | 13 | Hs.181357 |
| Breast GeneFilter | 13.56254 | 12.69236 | 536.6718 | 1184.14 | 1 | H | 4 | 23 | Hs.77385 |
| Breast GeneFilter | 13.56254 | 12.69236 | 1811.95 | 3834.971 | 1 | H | 5 | 26 | Hs.82646 |
| Breast GeneFilter | 13.56254 | 12.69236 | 18.33607 | 11.89124 | 2 | A | 11 | 9 | Hs.9732 |
| Breast GeneFilter | 13.56254 | 12.69236 | 2597.736 | 3847.6 | 2 | A | 10 | 22 | Hs.41007 |
| Breast GeneFilter | 13.56254 | 12.69236 | 72.63568 | 47.08278 | 2 | B | 2 | 27 | Hs.172801 |
| Breast GeneFilter | 13.56254 | 12.69236 | 15.70985 | 21.11957 | 2 | C | 8 | 4 | Hs.107325 |
| Breast GeneFilter | 13.56254 | 12.69236 | 376.6325 | 497.4136 | 2 | C | 9 | 20 | Hs.25600 |
| Breast GeneFilter | 13.56254 | 12.69236 | 1411.844 | 1994.42 | 2 | C | 2 | 23 | Hs.155979 |
| Breast GeneFilter | 13.56254 | 12.69236 | 67.77326 | 104.8175 | 2 | D | 2 | 8 | Hs.138671 |
| Breast GeneFilter | 13.56254 | 12.69236 | 62.43242 | 38.44348 | 2 | D | 12 | 21 | Hs.196914 |
| Breast GeneFilter | 13.56254 | 12.69236 | 208.0544 | 112.4615 | 2 | E | 2 | 8 | Hs.113368 |
| Breast GeneFilter | 13.56254 | 12.69236 | 330.8748 | 184.9721 | 2 | E | 3 | 17 | Hs.172153 |
| Breast GeneFilter | 13.56254 | 12.69236 | 122.224 | 188.4318 | 2 | E | 9 | 29 | Hs.7489 |
| Breast GeneFilter | 13.56254 | 12.69236 | 16.32129 | 11.35158 | 2 | G | 12 | 30 | Hs.184967 |
| Breast GeneFilter | 13.56254 | 12.69236 | 384.1351 | 682.7194 | 2 | H | 8 | 8 | Hs.31396 |
| Breast GeneFilter | 13.56254 | 12.69236 | 285.0607 | 565.8192 | 2 | H | 6 | 13 | Hs.53656 |
| Breast GeneFilter | 13.56254 | 12.69236 | 78.09672 | 130.7549 | 2 | H | 3 | 18 | Hs.159860 |

| Filter Type GF 225 | title | gene | NormInt1 SKBR3-ANEX+ve | NormInt2 SKBR3-ANEX–ve | Ratio | Diff |
|---|---|---|---|---|---|---|
| Breast GeneFilter | ARP2/3 protein complex subunit p41 | ARC41 | 1986.871 | 999.9936 | 1.9868834 | 986.88 |
| Breast GeneFilter | KRAB-associated protein 1 | TIF1B | 3738.21 | 2162.745 | 1.72845626 | 1575.47 |
| Breast GeneFilter | non-histone chromosome protein 2 (*S. cerevisiae*)-like 1 | NHP2L1 | 5832.062 | 2761.361 | 2.03959608 | 2870.7 |
| Breast GeneFilter | immunoglobulin superfamily, member 3 | IGSF3 | 30666.62 | 49893.25 | −1.62695646 | −19226.6 |
| Breast GeneFilter | Human mRNA for phM5 protein | — | 124362.2 | 196881.8 | −1.58313227 | −72519.6 |
| Breast GeneFilter | MAX binding protein | MNT | 3453.881 | 6214.475 | −1.79927301 | −2760.59 |
| Breast GeneFilter | branched chain alpha-ketoacid dehydrogenase kinase | BCKDK | 2470.064 | 4062.402 | −1.64465415 | −1592.34 |
| Breast GeneFilter | midkine (neurite growth-promoting factor 2) | MDK | 25177.52 | 38379.16 | −1.52434206 | −13201.6 |
| Breast GeneFilter | leukocyte immunoglobulin-like receptor | MIR-10 | 4440.301 | 7265.941 | −1.63636231 | −2825.64 |
| Breast GeneFilter | CDC28 protein kinase 1 | CKS1 | 130600.9 | 205.703 | −1.57505095 | −75102.1 |
| Breast GeneFilter | ephrin-B1 | EFNB1 | 3085.522 | 4834.966 | −1.56698489 | −1749.44 |
| Breast GeneFilter | ribosomal protein L19 | RPL19 | 1647.476 | 848.8703 | 1.94078612 | 918.61 |
| Breast GeneFilter | Human MDA-7 (mda-7) mRNA, complete cds | — | 76550.27 | 116918.7 | −4.52734542 | −10368.4 |
| Breast GeneFilter | polymerase (RNA) II (DNA directed) polypeptide E (25kD) | POLR2E | 1863.169 | 3279.23 | −1.760028 | −1416.06 |
| Breast GeneFilter | ribosomal protein S27 (metallopanstimulin 1) | RPS27 | 4627.264 | 2690.311 | 1.71997368 | 1936.95 |
| Breast GeneFilter | ras homolog gene family, member A | ARHA | 3187.677 | 1665.914 | 1.91347051 | 1521.76 |
| Breast GeneFilter | *H. sapiens* MLN51 mRNA | — | 11694.91 | 20600.61 | −1.76150262 | −8905.7 |
| Breast GeneFilter | tumor protein D52 | TPD52 | 4818.948 | 2671.486 | 1.80384541 | 2147.46 |
| Breast GeneFilter | purine-rich element binding protein A | PURA | 2670.883 | 4255.516 | −1.59329927 | −1584.63 |
| Breast GeneFilter | multiple endocrine neoplasia I | MEN1 | 6329.027 | 10513.86 | −1.66121292 | −4184.83 |
| Breast GeneFilter | GCN5 (general control of amino-acid synthesis, yeast, homolo | GCN5L1 | 16570 | 26199.65 | −1.58115005 | −9629.65 |
| Breast GeneFilter | Human mRNA for KIAA0276 gene, partial cds | — | 3732.4 | 8136.724 | −2.18002462 | −4404.32 |
| Breast GeneFilter | laminin receptor 1 (67kD); Ribosomal protein SA | LAMR1 | 22983.7 | 14350.97 | 1.60154343 | 8632.73 |
| Breast GeneFilter | Human non-muscle myosin alkali light chain mRNA, 3' end | — | 17062.81 | 30796.93 | −1.80491519 | −13734.1 |
| Breast GeneFilter | heat shock 40kD protein 1 | HSPF1 | 57608.71 | 99739.32 | −1.73123272 | −42130.6 |

TABLE 1-continued

SKBR3 Anexve–veSynFilComplR1.5.B&W.xls
Comparative differential gene expression analysis of SKBR3- Annexin positive (SKBR3-ANEX+ve) cells
versus SKBR3- Annexin negative (SKBR3-ANEX–ve) cells revealed that 40 genes had
significantly altered leveles of expression by 1.5-fold or greater. Of these 14 & 26 genes were found to be
differentially expressed in the SKBR3- Annexin positive and SKBR3- Annexin negative cells, respectively.

| | | | | | | |
|---|---|---|---|---|---|---|
| Breast GeneFilter | ESTs, Weakly similar to !!!! ALU SUBFAMILY J WARNING E | — | 426.0522 | 282.9269 | 1.50587392 | 143.13 |
| Breast GeneFilter | ESTs, Weakly similar to (define not available 3880849) [C. ele | — | 60360.32 | 91545.48 | −1.51664996 | −31185.2 |
| Breast GeneFilter | isoleucine-tRNA synthetase | IARS | 2876.156 | 1777.693 | 1.61791492 | 1098.46 |
| Breast GeneFilter | ESTs | — | 577.6293 | 893.7206 | −1.54722166 | −316.09 |
| Breast GeneFilter | ESTs | — | 13848.25 | 21049.14 | −1.51998568 | −7200.89 |
| Breast GeneFilter | Human mRNA for KIAA0295 gene, partial cds | — | 51911.51 | 84398.23 | −1.62580955 | −32486.7 |
| Breast GeneFilter | fms-related tyrosine kinase 1 (vascular endothelial growth fact | FLT1 | 2493.025 | 3850.02 | −1.54431641 | −1356.99 |
| Breast GeneFilter | ESTs | — | 2296.563 | 1412.056 | 1.62639689 | 844.51 |
| Breast GeneFilter | guanine nucleotide binding protein (G protein), alpha stimulatin | GNAS1 | 7321.198 | 3936.93 | 1.85962093 | 3384.27 |
| Breast GeneFilter | glutathione peroxidase 3 (plasma) | GPX3 | 11643.11 | 6475.298 | 1.79808021 | 5167.81 |
| Breast GeneFilter | ESTs | — | 4300.923 | 6596.413 | −1.53372014 | −2295.49 |
| Breast GeneFilter | ESTs | — | 663.6732 | 424.2502 | 1.56434357 | 239.42 |
| Breast GeneFilter | ESTs | — | 13675.82 | 23745.72 | −1.73632944 | −10069.9 |
| Breast GeneFilter | ESTs | — | 10148.61 | 19679.81 | −1.93916249 | −9531.2 |
| Breast GeneFilter | ESTs | — | 2780.366 | 4547.796 | −1.63568234 | −1767.43 |

TABLE 2

80060899BREANEXve-veSynFilComplR1.5.B&W.xls
Comparative differential gene expression analysis of #80060899BRE-Annexin positive (#80060899BRE-ANEX+ve) cells
versus #80060899BRE-Annexin negative (#80060899BRE-ANEX–ve) cells revealed that 63 genes had
significantly altered leveles of expression by 1.5-fold or greater. All of these genes were found to be
differentially expressed in the #80060899BRE-Annexin positive cells.

| TableName | FilterType GF225 | Head1_BGAvg #80060899BRE-ANEX+ve | Head2_BGAvg #80060899BRE-ANEX–ve | Data1_RawIntensity #80060899BRE-ANEX+ve | Data2_RawIntensity #80060899BRE-ANEX–ve |
|---|---|---|---|---|---|
| GF225 | Breast GeneFilter | 12.16622 | 12.89396 | 702.05 | 488.1645 |
| GF225 | Breast GeneFilter | 12.16622 | 12.89396 | 1011.696 | 636.6229 |
| GF225 | Breast GeneFilter | 12.16622 | 12.89396 | 265.7989 | 133.0044 |
| GF225 | Breast GeneFilter | 12.16622 | 12.89396 | 98.7685 | 75.77792 |
| GF225 | Breast GeneFilter | 12.16622 | 12.89396 | 543.7198 | 330.2836 |
| GF225 | Breast GeneFilter | 12.16622 | 12.89396 | 146.1391 | 114.645 |
| GF225 | Breast GeneFilter | 12.16622 | 12.89396 | 76.26098 | 55.45963 |
| GF225 | Breast GeneFilter | 12.16622 | 12.89396 | 421.2297 | 345.7194 |
| GF225 | Breast GeneFilter | 12.16622 | 12.89396 | 236.2751 | 167.1667 |
| GF225 | Breast GeneFilter | 12.16622 | 12.89396 | 257.5699 | 186.8602 |
| GF225 | Breast GeneFilter | 12.16622 | 12.89396 | 3749.604 | 2892.917 |
| GF225 | Breast GeneFilter | 12.16622 | 12.89396 | 201.3526 | 126.1709 |
| GF225 | Breast GeneFilter | 12.16622 | 12.89396 | 1022.082 | 730.9009 |
| GF225 | Breast GeneFilter | 12.16622 | 12.89396 | 217.6139 | 116.498 |
| GF225 | Breast GeneFilter | 12.16622 | 12.89396 | 2595.324 | 1575.159 |
| GF225 | Breast GeneFilter | 12.16622 | 12.89396 | 109.9706 | 86.00154 |
| GF225 | Breast GeneFilter | 12.16622 | 12.89396 | 156.5695 | 115.531 |
| GF225 | Breast GeneFilter | 12.16622 | 12.89396 | 1730.067 | 1305.118 |
| GF225 | Breast GeneFilter | 12.16622 | 12.89396 | 937.867 | 672.9494 |
| GF225 | Breast GeneFilter | 12.16622 | 12.89396 | 141.4012 | 114.6111 |
| GF225 | Breast GeneFilter | 12.16622 | 12.89396 | 614.5146 | 513.2037 |
| GF225 | Breast GeneFilter | 12.16622 | 12.89396 | 174.0228 | 128.9007 |
| GF225 | Breast GeneFilter | 12.16622 | 12.89396 | 1173.544 | 976.9803 |
| GF225 | Breast GeneFilter | 12.16622 | 12.89396 | 105.6052 | 78.61996 |
| GF225 | Breast GeneFilter | 12.16622 | 12.89396 | 106.472 | 80.64763 |
| GF225 | Breast GeneFilter | 12.16622 | 12.89396 | 416.1731 | 302.3279 |
| GF225 | Breast GeneFilter | 12.16622 | 12.89396 | 74.64893 | 56.23211 |
| GF225 | Breast GeneFilter | 12.16622 | 12.89396 | 32.11365 | 21.7196 |
| GF225 | Breast GeneFilter | 12.16622 | 12.89396 | 1940.258 | 1276.052 |
| GF225 | Breast GeneFilter | 12.16622 | 12.89396 | 229.0105 | 181.325 |
| GF225 | Breast GeneFilter | 12.16622 | 12.89396 | 658.1039 | 504.0877 |
| GF225 | Breast GeneFilter | 12.16622 | 12.89396 | 157.5227 | 133.8199 |
| GF225 | Breast GeneFilter | 12.16622 | 12.89396 | 243.0308 | 216.6431 |
| GF225 | Breast GeneFilter | 12.16622 | 12.89396 | 589.0263 | 520.9788 |
| GF225 | Breast GeneFilter | 12.16622 | 12.89396 | 574.3094 | 512.2259 |
| GF225 | Breast GeneFilter | 12.16622 | 12.89396 | 397.9135 | 332.7921 |
| GF225 | Breast GeneFilter | 12.16622 | 12.89396 | 432.522 | 347.6953 |
| GF225 | Breast GeneFilter | 12.16622 | 12.89396 | 1276.832 | 1120.96 |
| GF225 | Breast GeneFilter | 12.16622 | 12.89396 | 2904.885 | 2262.511 |
| GF225 | Breast GeneFilter | 12.16622 | 12.89396 | 494.9388 | 380.2501 |
| GF225 | Breast GeneFilter | 12.16622 | 12.89396 | 110.3552 | 71.43282 |
| GF225 | Breast GeneFilter | 12.16622 | 12.89396 | 103.4821 | 59.63686 |

TABLE 2-continued

80060899BREANEXve-veSynFilComplR1.5.B&W.xls
Comparative differential gene expression analysis of #80060899BRE-Annexin positive (#80060899BRE-ANEX+ve) cells versus #80060899BRE-Annexin negative (#80060899BRE-ANEX−ve) cells revealed that 63 genes had significantly altered leveles of expression by 1.5-fold or greater. All of these genes were found to be differentially expressed in the #80060899BRE-Annexin positive cells.

| | | | | | |
|---|---|---|---|---|---|
| GF225 | Breast GeneFilter | 12.16622 | 12.89396 | 2432.994 | 1890.604 |
| GF225 | Breast GeneFilter | 12.16622 | 12.89396 | 748.2268 | 469.9998 |
| GF225 | Breast GeneFilter | 12.16622 | 12.89396 | 838.4484 | 590.2916 |
| GF225 | Breast GeneFilter | 12.16622 | 12.89396 | 3341.728 | 2201.421 |
| GF225 | Breast GeneFilter | 12.16622 | 12.89396 | 178.9771 | 100.5989 |
| GF225 | Breast GeneFilter | 12.16622 | 12.89396 | 121.6087 | 95.55091 |
| GF225 | Breast GeneFilter | 12.16622 | 12.89396 | 1549.878 | 1144.886 |
| GF225 | Breast GeneFilter | 12.16622 | 12.89396 | 189.649 | 138.4131 |
| GF225 | Breast GeneFilter | 12.16622 | 12.89396 | 306.0685 | 255.746 |
| GF225 | Breast GeneFilter | 12.16622 | 12.89396 | 116.2641 | 84.69499 |
| GF225 | Breast GeneFilter | 12.16622 | 12.89396 | 365.4977 | 290.1935 |
| GF225 | Breast GeneFilter | 12.16622 | 12.89396 | 2048.506 | 1694.005 |
| GF225 | Breast GeneFilter | 12.16622 | 12.89396 | 485.7777 | 400.9786 |
| GF225 | Breast GeneFilter | 12.16622 | 12.89396 | 679.442 | 554.5363 |
| GF225 | Breast GeneFilter | 12.16622 | 12.89396 | 1038.763 | 809.8124 |
| GF225 | Breast GeneFilter | 12.16622 | 12.89396 | 437.1326 | 317.3184 |
| GF225 | Breast GeneFilter | 12.16622 | 12.89396 | 352.3212 | 196.1996 |
| GF225 | Breast GeneFilter | 12.16622 | 12.89396 | 34.98531 | 25.10817 |
| GF225 | Breast GeneFilter | 12.16622 | 12.89396 | 157.6186 | 103.6439 |
| GF225 | Breast GeneFilter | 12.16622 | 12.89396 | 386.0974 | 248.6657 |
| GF225 | Breast GeneFilter | 12.16622 | 12.89396 | 315.2936 | 175.1065 |

| TableName | field | grid | col | row | cluster id | title |
|---|---|---|---|---|---|---|
| GF225 | 1 | A | 6 | 4 | Hs.80475 | polymerase (RNA) II (DNA directed) polypeptide J (13.3kD) |
| GF225 | 1 | A | 7 | 5 | Hs.8765 | *Homo sapiens* RNA helicase-related protein mRNA, complete cds |
| GF225 | 1 | A | 11 | 6 | Hs.75415 | beta-2-microglobulin |
| GF225 | 1 | A | 6 | 8 | Hs.115617 | corticotropin releasing hormone-binding protein |
| GF225 | 1 | A | 8 | 11 | Hs.14839 | polymerase (RNA) II (DNA directed) polypeptide G |
| GF225 | 1 | A | 7 | 12 | Hs.16232 | connector enhancer of KSR-like (Drosophila kinase suppressor of ras) |
| GF225 | 1 | A | 9 | 17 | Hs.79339 | lectin, galactoside-binding, soluble, 3 binding protein (galectin 6 bindin |
| GF225 | 1 | A | 11 | 17 | Hs.119387 | KIAA0792 gene product |
| GF225 | 1 | A | 12 | 19 | Hs.112193 | mutS (*E. coli*) homolog 5 |
| GF225 | 1 | A | 12 | 25 | Hs.180780 | *Homo sapiens* agrin precursor mRNA, partial cds |
| GF225 | 1 | A | 8 | 29 | Hs.75841 | *Homo sapiens* mRNA for ERp28 protein |
| GF225 | 1 | A | 5 | 30 | Hs.808 | heterogeneous nuclear ribonucleoprotein F |
| GF225 | 1 | A | 7 | 30 | Hs.184601 | solute carrier family 7 (cationic amino acid transporter, y+ system), mer |
| GF225 | 1 | C | 9 | 2 | Hs.203502 | secretory leukocyte protease inhibitor (antileukoproteinase) |
| GF225 | 1 | C | 8 | 4 | Hs.214198 | Human mRNA for pM5 protein |
| GF225 | 1 | C | 5 | 14 | Hs.11465 | glutathione-S-transferase like |
| GF225 | 1 | C | 3 | 25 | Hs.78068 | carboxypeptidase Z |
| GF225 | 1 | D | 9 | 3 | Hs.179661 | *Homo sapiens* clone 24703 beta-tubulin mRNA, complete cds |
| GF225 | 1 | D | 5 | 9 | Hs.170008 | methylmalonate-semialdehyde dehydrogenase |
| GF225 | 1 | F | 7 | 7 | Hs.83363 | Human nested gene protein gene, complete cds |
| GF225 | 1 | F | 6 | 21 | Hs.84084 | amyloid beta precursor protein (cytoplasmic tail)-binding protein 2 |
| GF225 | 1 | F | 2 | 29 | Hs.214197 | plasminogen activator, tissue |
| GF225 | 1 | G | 7 | 14 | Hs.75742 | matrix Gla protein |
| GF225 | 1 | G | 8 | 29 | Hs.180347 | carcinoembryonic antigen |
| GF225 | 1 | H | 6 | 4 | Hs.135084 | cystatin C (amyloid angiopathy and cerebral hemorrhage) |
| GF225 | 1 | H | 10 | 5 | Hs.146688 | microsomal glutathione S-transferase 1-like 1 |
| GF225 | 1 | H | 11 | 6 | Hs.119251 | ubiquinol-cytochrome c reductase core protein I |
| GF225 | 1 | H | 11 | 9 | Hs.26002 | LIM domain binding 1 |
| GF225 | 1 | H | 12 | 10 | Hs.5372 | claudin 4 |
| GF225 | 1 | H | 12 | 11 | Hs.154737 | *Homo sapiens* serine protease mRNA, complete cds |
| GF225 | 1 | H | 12 | 13 | Hs.108809 | chaperonin containing TCP1, subunit 7 (eta) |
| GF225 | 1 | H | 8 | 18 | Hs.83919 | Glucosidase I |
| GF225 | 1 | H | 2 | 21 | Hs.204238 | lipocalin 2 (oncogene 24p3) |
| GF225 | 1 | H | 12 | 22 | Hs.10326 | *Homo sapiens* mRNA for Epsilon COP |
| GF225 | 1 | H | 4 | 23 | Hs.77385 | Human non-muscle myosin alkali light chain mRNA, 3' end |
| GF225 | 1 | H | 12 | 24 | Hs.102824 | tropomyosin 4 |
| GF225 | 1 | H | 12 | 25 | Hs.82109 | syndecan 1 |
| GF225 | 1 | H | 12 | 28 | Hs.6396 | *Homo sapiens* hJTB mRNA, complete cds |
| GF225 | 2 | A | 8 | 5 | Hs.97176 | ESTs |
| GF225 | 2 | A | 2 | 8 | Hs.181165 | eukaryotic translation elongation factor 1 alpha 1 |
| GF225 | 2 | A | 7 | 9 | Hs.112242 | ESTs |
| GF225 | 2 | A | 12 | 10 | Hs.40780 | ESTs |
| GF225 | 2 | A | 8 | 13 | Hs.169388 | ESTs |
| GF225 | 2 | A | 2 | 14 | Hs.74562 | Human siah binding protein 1 (SiahBP1) mRNA, partial cds |
| GF225 | 2 | A | 9 | 17 | Hs.165743 | ESTs, Highly similar to (define not available 4567068) [*H. sapiens*] |
| GF225 | 2 | A | 10 | 22 | Hs.41007 | ESTs, Weakly similar to (define not available 3880849) [*C. elegans*] |
| GF225 | 2 | A | 12 | 22 | Hs.72132 | ESTs |
| GF225 | 2 | A | 10 | 28 | Hs.97272 | ESTs |
| GF225 | 2 | B | 10 | 16 | Hs.32360 | ESTs, Weakly similar to KIAA0454 protein [*H. sapiens*] |

TABLE 2-continued

80060899BREANEXve-veSynFilComplR1.5.B&W.xls
Comparative differential gene expression analysis of #80060899BRE-Annexin positive (#80060899BRE-ANEX+ve) cells versus #80060899BRE-Annexin negative (#80060899BRE-ANEX−ve) cells revealed that 63 genes had significantly altered leveles of expression by 1.5-fold or greater. All of these genes were found to be differentially expressed in the #80060899BRE-Annexin positive cells.

| | | | | | | |
|---|---|---|---|---|---|---|
| GF225 | 2 | B | 4 | 22 | Hs.206654 | ESTs, Moderately similar to !!!! ALU SUBFAMILY SQ WARNING ENTR |
| GF225 | 2 | C | 10 | 14 | Hs.8135 | ESTs |
| GF225 | 2 | C | 12 | 27 | Hs.159986 | EST |
| GF225 | 2 | D | 7 | 27 | Hs.183211 | ESTs, Weakly similar to similar to collagen [C. elegans] |
| GF225 | 2 | E | 6 | 20 | Hs.103938 | ESTs |
| GF225 | 2 | E | 9 | 27 | Hs.11747 | ESTs |
| GF225 | 2 | G | 4 | 7 | Hs.144978 | ESTs |
| GF225 | 2 | G | 7 | 9 | Hs.10098 | ESTs, Weakly similar to RCK [H. sapiens] |
| GF225 | 2 | G | 3 | 10 | Hs.93557 | proenkephalin |
| GF225 | 2 | G | 6 | 13 | Hs.45109 | ESTs |
| GF225 | 2 | H | 8 | 3 | Hs.108255 | ESTs, Highly similar to MEM3 [M. musculus] |
| GF225 | 2 | H | 4 | 11 | Hs.146059 | ESTs |
| GF225 | 2 | H | 6 | 13 | Hs.53656 | ESTs |
| GF225 | 2 | H | 5 | 25 | Hs.111968 | ESTs |

| TableName | gene | NormInt1 #80060899BRE-ANEX+ve | NormInt2 #80060899BRE-ANEX−ve | Ratio | Diff |
|---|---|---|---|---|---|
| GF225 | POLR2J | 29258.06 | 16347.19 | 1.789791 | 12910.9 |
| GF225 | — | 42162.63 | 21318.63 | 1.977736 | 20844 |
| GF225 | B2M | 11077.21 | 4453.925 | 2.487068 | 6623.29 |
| GF225 | CRHBP | 4116.195 | 2537.58 | 1.622095 | 1578.62 |
| GF225 | POLR2G | 22659.62 | 11060.23 | 2.048748 | 11599.4 |
| GF225 | CNK1 | 6090.372 | 3839.125 | 1.586396 | 2251.25 |
| GF225 | LGALS3BP | 3178.19 | 1857.18 | 1.711299 | 1321.01 |
| GF225 | KIAA0792 | 17554.82 | 11577.13 | 1.516337 | 5977.7 |
| GF225 | MSH5 | 9846.806 | 5597.921 | 1.759011 | 4248.88 |
| GF225 | — | 10734.27 | 6257.397 | 1.715453 | 4476.88 |
| GF225 | — | 156265.4 | 96875.27 | 1.613058 | 59390.2 |
| GF225 | HNRPF | 8391.408 | 4225.091 | 1.986089 | 4166.32 |
| GF225 | SLC7A5 | 42595.46 | 24475.72 | 1.740315 | 18119.7 |
| GF225 | SLPI | 14072.85 | 6415.639 | 2.193523 | 7657.22 |
| GF225 | — | 167836.8 | 86745.27 | 1.934824 | 81091.5 |
| GF225 | GSTTLp28 | 7111.677 | 4736.173 | 1.501566 | 2375.5 |
| GF225 | CPZ | 10125.18 | 6362.385 | 1.591413 | 3762.79 |
| GF225 | — | 92636.98 | 61654.04 | 1.502529 | 30982.9 |
| GF225 | MMSDH | 50218.4 | 31790.26 | 1.579679 | 18428.1 |
| GF225 | — | 7019.64 | 4500.866 | 1.55962 | 2518.77 |
| GF225 | APPBP2 | 30506.6 | 20153.9 | 1.513682 | 10352.7 |
| GF225 | PLAT | 8639.085 | 5062.028 | 1.706645 | 3577.06 |
| GF225 | MGP | 59679.07 | 39540.87 | 1.509301 | 20138.2 |
| GF225 | CEA | 5370.416 | 3181.949 | 1.687775 | 2188.47 |
| GF225 | CST3 | 5174.043 | 2898.465 | 1.785098 | 2275.58 |
| GF225 | MGST1L1 | 20224.07 | 10865.62 | 1.86129 | 9358.45 |
| GF225 | UQCRC1 | 3627.59 | 2020.974 | 1.794971 | 1606.62 |
| GF225 | LDB1 | 1560.573 | 780.5994 | 1.999199 | 779.97 |
| GF225 | CLDN4 | 94287.46 | 45861.14 | 2.055933 | 48426.3 |
| GF225 | — | 11128.84 | 6516.796 | 1.707716 | 4612.04 |
| GF225 | CCT7 | 31980.78 | 18116.84 | 1.765251 | 13863.9 |
| GF225 | GCS1 | 7654.867 | 4809.47 | 1.591624 | 2845.4 |
| GF225 | LCN2 | 11810.16 | 7786.123 | 1.516822 | 4024.04 |
| GF225 | — | 28623.93 | 18723.91 | 1.528737 | 9900.02 |
| GF225 | — | 27908.75 | 18409.33 | 1.516012 | 9499.43 |
| GF225 | TPM4 | 19336.74 | 11960.5 | 1.616716 | 7376.24 |
| GF225 | SDC1 | 21018.55 | 12496.12 | 1.682006 | 8522.43 |
| GF225 | — | 62048.07 | 40287.14 | 1.540146 | 21760.9 |
| GF225 | — | 101850.6 | 63786.51 | 1.596742 | 38064.1 |
| GF225 | EEF1A1 | 17353.46 | 10720.32 | 1.618746 | 6633.15 |
| GF225 | — | 3869.256 | 2013.891 | 1.921283 | 1855.36 |
| GF225 | — | 3628.273 | 1681.33 | 2.157978 | 1946.94 |
| GF225 | — | 85305.26 | 53301.41 | 1.600432 | 32003.9 |
| GF225 | — | 26234.21 | 13250.61 | 1.979849 | 12983.6 |
| GF225 | — | 29397.54 | 16641.97 | 1.76647 | 12755.6 |
| GF225 | — | 117167.1 | 62064.23 | 1.887837 | 55102.9 |
| GF225 | — | 6275.266 | 2836.166 | 2.212588 | 3439.1 |
| GF225 | — | 4263.826 | 2693.848 | 1.582801 | 1569.98 |
| GF225 | — | 75336.98 | 50123.38 | 1.503031 | 25213.6 |
| GF225 | — | 9218.518 | 6059.759 | 1.521268 | 3158.76 |
| GF225 | — | 17991.39 | 11934.77 | 1.507477 | 6056.62 |
| GF225 | — | 6834.264 | 3952.42 | 1.729134 | 2881.84 |
| GF225 | — | 18792.14 | 11868.46 | 1.583367 | 6923.68 |
| GF225 | — | 99663.57 | 66037.28 | 1.509202 | 33626.3 |

TABLE 2-continued

80060899BREANEXve-veSynFilComplR1.5.B&W.xls
Comparative differential gene expression analysis of #80060899BRE-Annexin positive (#80060899BRE-ANEX+ve) cells
versus #80060899BRE-Annexin negative (#80060899BRE-ANEX–ve) cells revealed that 63 genes had
significantly altered leveles of expression by 1.5-fold or greater. All of these genes were found to be
differentially expressed in the #80060899BRE-Annexin positive cells.

| | | | | | |
|---|---|---|---|---|---|
| GF225 | — | 23633.98 | 15631.32 | 1.511963 | 8002.66 |
| GF225 | — | 35519.65 | 22940.63 | 1.548329 | 12579 |
| GF225 | — | 54304.11 | 33501.16 | 1.620962 | 20803 |
| GF225 | PENK | 22852.28 | 13127.16 | 1.74084 | 9725.12 |
| GF225 | — | 18418.54 | 8116.587 | 2.269246 | 10302 |
| GF225 | — | 1563.57 | 971.0319 | 1.610215 | 592.54 |
| GF225 | — | 7044.317 | 4008.319 | 1.757424 | 3036 |
| GF225 | — | 17255.54 | 9616.882 | 1.794297 | 7638.66 |
| GF225 | — | 14091.16 | 6772.059 | 2.080779 | 7319.1 |

We claim:

1. A method for separating living neoplastic cells that are resistant to a cytotoxic compound from dead cells, living stromal cells and living neoplastic cells that are sensitive to the cytotoxic compound in a mixed population of cells from a tumor sample, the method comprising the steps of:
 a) contacting the mixed population of cells with the cytotoxic compound for a time and at a concentration wherein the stromal cells and neoplastic cells that are sensitive to the cytotoxic compound undergo apoptosis;
 b) contacting the mixed population of step (a) with a vital stain or fluorescent dye;
 c) contacting the mixed population of cells of step (b) with Annexin V;
 d) contacting the mixed cell population of step (c) with a detectably-labeled immunological reagent that specifically binds to Annexin V; and
 e) selecting the cells in the mixed population of step (c) that are not stained with the vital stain and that do not bind the immunological reagent.

2. The method of claim 1, wherein the vital stain is propidium iodide.

3. The method of claim 2, wherein the immunological reagent that specifically binds to Annexin V is detectably labeled with a fluorescent label.

4. The method of claim 2, wherein the cells of step (c) are selected by fluorescence-activated cell sorting.

5. The method of claim 2, wherein the mixed population is contacted with the cytotoxic compound under in vitro cell culture conditions whereby the cells cannot attach to a solid substrate.

6. The method of claim 2, wherein the tumor sample is a solid tumor sample and the mixed cell population is a disaggregated tumor sample.

7. The method of claim 2, wherein the tumor sample is a hematopoietic tumor sample and the mixed cell population is a nucleated hematopoietic cell sample.

8. A method for detecting a gene expression profile of living neoplastic cells that are resistant to a cytotoxic compound and distinguishing said profile from the gene expression profile of living neoplastic cells that are sensitive to the cytotoxic compound in a mixed population of cells from a tumor sample, the method comprising the steps of:
 a) contacting the mixed population of cells with the cytotoxic compound for a time and at a concentration wherein the neoplastic cells that are sensitive to the cytotoxic compound undergo apoptosis;
 b) contacting the mixed population of step (a) with a vital stain or fluorescent dye;
 c) contacting the mixed population of cells of step (b) with Annexin V;
 d) contacting the mixed cell population of step (c) with a detectably-labeled immunological reagent that specifically binds to Annexin V; and
 e) separating the cells in the mixed population of step (d) that are not stained with the vital stain from the cells that are stained with the vital stain;
 f) separating the cells in the mixed population of step (e) that are not stained with the vital stain and that do not bind the immunological reagent from the cells in the mixed population of step (c) that are not stained with the vital stain and that do bind the immunological reagent;
 g) isolating cellular RNA from the each of the separated cells selected in step (f);
 h) preparing detectably-labeled CDNA from the cellular RNA isolated in step (g);
 i) hybridizing each of the cDNA preparations prepared in step (h) to a gene array comprising at least 4000 eukaryotic genes;
 j) detecting a pattern of gene expression for hybridization of each of the CDNA preparations prepared from the mRNA isolated from the cells selected in step (f); and
 k) comparing the pattern of gene expression detected in step (j) from hybridization of the microarray with CDNA from cells that are not stained with the vital stain and that do not bind the immunological reagent with a pattern of gene expression obtained by hybridizing CDNA prepared from cells that are not stained with the vital stain and that do bind the immunological reagent.

9. The method of claim 8, wherein the vital stain is propidium iodide.

10. The method of claim 8, wherein the immunological reagent that specifically binds to Annexin V is detectably labeled with a fluorescent label.

11. The method of claim 8, wherein the cells of step (f) are selected by fluorescence-activated cell sorting.

12. The method of claim 8, wherein the cytotoxic compound is a chemotherapeutic drug.

13. The method of claim 8, wherein the cDNA is detectably labeled with a fluorescent label.

14. The method of claim 9, wherein the mixed population is contacted with the cytotoxic compound under in vitro cell culture conditions whereby the cells cannot attach to a solid substrate.

15. The method of claim 9, wherein the tumor sample is a solid tumor sample and the mixed cell population is a disaggregated tumor sample.

16. The method of claim 9, wherein the tumor sample is a hematopoietic tumor sample and the mixed cell population is a nucleated hematopoietic cell sample.

* * * * *